United States Patent
Hoener et al.

(10) Patent No.: US 10,457,644 B2
(45) Date of Patent: Oct. 29, 2019

(54) PYRAZOL COMPOUNDS AS EAAT3 INHIBITORS

(71) Applicant: Hoffmann-La Roche Inc., Little Falls, NJ (US)

(72) Inventors: Marius Hoener, Basel (CH); Juergen Wichmann, Basel (CH)

(73) Assignee: Hoffman-La Roche Inc., Little Falls, NJ (US)

(*) Notice: Subject to any disclaimer, the term of this patent is extended or adjusted under 35 U.S.C. 154(b) by 0 days.

(21) Appl. No.: 16/195,441

(22) Filed: Nov. 19, 2018

(65) Prior Publication Data

US 2019/0119218 A1    Apr. 25, 2019

Related U.S. Application Data

(63) Continuation of application No. PCT/EP2017/062512, filed on May 24, 2017.

(30) Foreign Application Priority Data

May 27, 2016   (EP) .................................... 16171680

(51) Int. Cl.
C07D 231/12   (2006.01)
(52) U.S. Cl.
CPC ................... C07D 231/12 (2013.01)
(58) Field of Classification Search
None
See application file for complete search history.

(56) References Cited

U.S. PATENT DOCUMENTS

| | | |
|---|---|---|
| 10,005,736 B1 | 6/2018 | Hoener et al. |
| 2009/0163499 A1 | 6/2009 | Chen et al. |

FOREIGN PATENT DOCUMENTS

| | | |
|---|---|---|
| JP | 2006-151954 A | 6/2006 |
| JP | 2010-540585 A | 12/2010 |
| JP | 2011-528658 A | 11/2011 |
| WO | 2007/042545 A1 | 4/2007 |
| WO | 2008/000645 A1 | 1/2008 |
| WO | 2009/043780 A1 | 4/2009 |
| WO | 2009/077366 A1 | 6/2009 |
| WO | 2009/077367 A1 | 6/2009 |
| WO | 2010/009062 A1 | 1/2010 |
| WO | 2010/051188 A1 | 5/2010 |
| WO | 2016/169902 A1 | 10/2016 |
| WO | 2016/193235 A1 | 12/2016 |
| WO | 2017/072083 A1 | 5/2017 |

OTHER PUBLICATIONS

Aoyama et al., "Neuronal glutathione deficiency and age-dependent neurodegeneration in the EAAC1 deficient mouse." Nat Neurosci. 9(1):119-126 ( 2006).

Bridges Richard J. et al., "The excitatory amino acid transporters: pharmacological insights on substrate and inhibitor specificity of the EAAT subtypes" Pharmacology & Therapeutics 107(3):271-285 (Sep. 1, 2005).
Greenfield Alexander et al., "Synthesis and biological activities of aryl-ether-, biaryl-, and fluorene-aspartic acid and diaminopropionic acid analogs as potent inhibitors of the high-affinity glutamate transporter EAAT-2" Bioorganic & Medicinal Chemistry Letters 15(22):4985-4988 (Nov. 14, 2005).
ISR of PCT/EP2016/058594 (Dated Jun. 24, 2016).
ISR of PCT/EP2016/062204 (Completed on Jul. 27, 2016).
ISR of PCT/EP2016/073589 (Completed Nov. 7, 2016).
ISR of PCT/EP2016/075590 (Completed on Jan. 19, 2017).
ISR of PCT/EP2017/051873 (Completed on Feb. 27, 2017).
ISR of PCT/EP2017/062512 (Completed on Jul. 11, 2017).
Jarzylo et al., "Parasynaptic NMDA Receptor Signaling Couples Neuronal Glutamate Transporter Function to AMPA Receptor Synaptic Distribution and Stabililty" The Journal of Neuroscience 32(7):2552-2563 ( 2012).
Jensen et al., "Excitatory amino acid transporters: recent insights into molecular mechanisms, novel modes of modulation and new therapeutic possibilities" Current Opinion in Pharmacology 20:116-123 (Feb. 1, 2015).
Jing et al. et al., "GFRα-2 and GFRα-3 Are Two New Receptors for Ligands of the GDNF Family" J Biol Chem 272(52):33111-33117 (Dec. 26, 1997).

(Continued)

Primary Examiner — Kamal A Saeed
(74) Attorney, Agent, or Firm — Mark D. Kafka

(57) ABSTRACT

The invention provides novel compounds having the general formula (I)

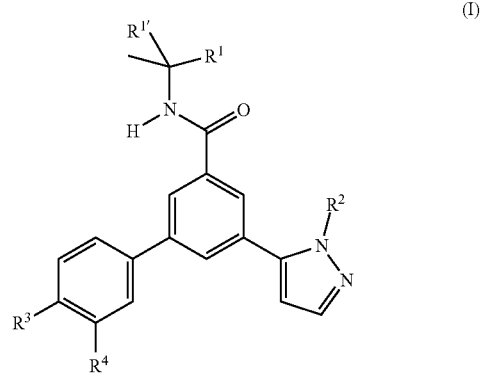

wherein $R^1$, $R^{1'}$, $R^2$, $R^3$, $R^4$ are as defined herein, compositions including the compounds and methods of using the compounds.

13 Claims, No Drawings

(56) References Cited

OTHER PUBLICATIONS

Mavencamp Terri L. et al., "Synthesis and preliminary pharmacological evaluation of novel derivatives of L-β-threo-benzylaspartate as inhibitors of the neuronal glutamate transporter EAAT3" Bioorganic & Medicinal Chemistry 16(16):7740-7748 (Aug. 15, 2008).
Nieoullon et al., "The neuronal excitatory amino acid transporter EAAC1/EAAT3: does it represent a major actor at the brain excitatory synapse?" Journal of Neurochemistry 98:1007-1018 ( 2006).
Product Sheets R&D Systems, Human FGF R3 (IIIb) Antibody, Monoclonal Mouse IgG$_1$ Clone #133111, MAB765 (downloaded Aug. 31, 2011).
Scimemi et al., "Neuronal Transporters Regulate Glutamate Clearance, NMDA Receptor Activation, and Synaptic Plasticity in the Hippocampus" The Journal of Neuroscience 29(46):14581-14595 ( 2009).
Wendland et al., "A Haplotype Containing Quantitative Trait Loci for SLC1A1 Gene Expression and Its Association With Obsessive-Compulsive Disorder" Arch Gen Psychiatry 66(4):408-416 ( 2009).

PYRAZOL COMPOUNDS AS EAAT3 INHIBITORS

CROSS-REFERENCE TO RELATED APPLICATIONS

This application is a continuation of, and claims priority to, International Patent Application No. PCT/EP2017/062512, filed on May 24, 2017. This application also claims priority to European Patent Application No. 16171680.8, filed on May 27, 2016. The entire contents of each of the above patent applications are hereby incorporated by reference.

The present invention relates to organic compounds useful for therapy or prophylaxis in a mammal, and in particular to EAAT3 inhibitors for the treatment or prophylaxis of EAAT3 mediated diseases, such as psychiatric disorders such as schizophrenia, bipolar disorder, obsessive-compulsive disorder or autism spectrum disorder.

The present invention provides novel compounds of formula (I)

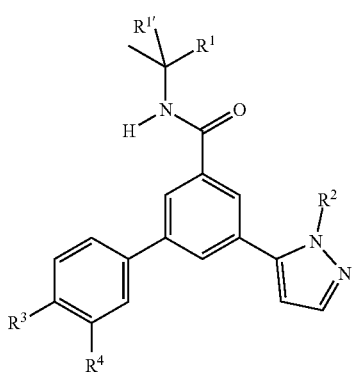

wherein
$R^{1'}$ is methyl;
$R^1$ is selected from the group consisting of
  i) methyl,
  ii) ethyl,
  iii) trifluoromethyl
  iv) hydroxymethyl,
  v) cyclopropyl, and
  vi) cyano;
or $R^{1'}$ and $R^1$ together with the carbon atom to which they are attached form 1,1-dioxo-tetrahydro-thiophen-3-yl;
$R^2$ is selected from the group consisting of
  i) hydrogen,
  ii) methyl,
  iii) ethyl,
  iv) isopropyl,
  v) tert-butyl,
  vi) cyclopropyl,
  vii) cyclopropylmethyl, and
  viii) hydroxymethyl;
$R^3$ is selected from the group consisting of
  i) hydrogen,
  ii) chloro,
  iii) fluoro,
  iv) methyl
  v) isopropyl,
  vi) methoxy,
  vii) cyano,
  viii) cyclopropyl, and
  ix) trifluoromethyl;
$R^4$ is selected from the group consisting of
  i) hydrogen,
  ii) chloro,
  iii) fluoro, and
  iv) methyl;
or pharmaceutically acceptable salts.

It has been surprisingly been found that the compounds of general formula I are EAAT3 inhibitors.

The excitatory amino acid transporter 3 (EAAT3), also referred to in human studies as solute carrier family 1, member 1 (systematic gene name: SLC1A1) and in rodents as excitatory amino acid carrier 1 (EAAC1), is a high-affinity anionic amino acid transporter found in neurons throughout the cortex and in the hippocampus, basal ganglia (striatum, thalamus), and the olfactory bulb. EAAT3 functions to buffer local glutamate concentrations at excitatory synapses, for example in the hippocampus, and modulates the differential recruitment of glutamate receptor subtypes at extrasynaptic sites. Furthermore, EAAT3 is thought to be involved in facilitating GABA and glutathione biosynthesis. EAAT3 is a member of the EAAT family that mediates the uptake of glutamate into neuronal and glial cells of the mammalian CNS. Two transporters expressed primarily in glia, EAAT1 and EAAT2, are crucial for glutamate homeostasis in the adult mammalian brain and for rapid clearance of glutamate from the synaptic cleft. Three neuronal transporters (EAAT3, EAAT4, and EAAT5) appear to have additional functions in regulating and processing cellular excitability with EAAT3 being abundantly expressed throughout the CNS (EAAT4 is unique to Purkinje cells of the cerebellum and EAAT5 is expressed in rod photoreceptor and bipolar cells of the retina).

EAATs are assembled as trimers, and the existence of multiple isoforms raises the question of whether certain isoforms can form hetero-oligomers. In the mammalian brain, the specificity of excitatory synaptic transmission depends on rapid diffusion of glutamate away from active synapses and the powerful uptake capacity of glutamate transporters in astrocytes. The extent to which neuronal glutamate transporters influence the lifetime of glutamate in the extracellular space remains unclear, but it is thought to be minor. EAAT3, the predominant neuronal glutamate transporter at excitatory synapses in hippocampal area CA1, buffers glutamate released during synaptic events and prolongs the time course of its clearance by astrocytes. EAAT3 does not significantly alter activation of receptors in the synaptic cleft. Instead, it reduces recruitment of perisynaptic/extrasynaptic NR2B-containing NMDARs, thereby facilitating induction of long-term potentiation by short bursts of high-frequency stimulation. Specific EAAT3 inhibitors may have the potential to locally and specifically strengthen particular synapses.

Obsessive-compulsive disorder (OCD) is among the most common mental disorders (prevalence 1-3%), and is at least as prevalent as schizophrenia and bipolar disorder. In the United States, one in 50 adults suffers from OCD. OCD affects children and adolescents as well as adults. Roughly one third to one half of adults with OCD reports a childhood onset of the disorder, and the disorder is typically chronic in nature. Treatment consists of predominantly serotonergic TCAs (clomipramine) or SSRIs in combination with cognitive-behavioral therapy (CBT). Overall, response to these interventions is of some but still limited benefit (approximately comparable to antidepressant response in MDD), and given the chronicity of OCD, the unmet medical need remains very high. OCD has been linked to serotonin and glutamate abnormalities. The hypothesis of glutamate signaling dysfunction in OCD is based on findings from neuroimaging, animal models, positional cloning and treatment studies.

The obsessive-compulsive symptomatology in OCD has considerable phenomenological, epidemiological and possibly (aetio)-pathophysiological overlap with a core autism spectrum disorder criterion: "restricted, repetitive patterns of behavior, interests, or activities" (taken from proposed DSM-5 revision). In support of this notion, human genetics studies have linked both the serotonin transporter and EAAT3 (SLC1A1) genes to autism spectrum disorder (ASD) or rigid-compulsive behavior in ASD and to OCD.

In addition, obsessive-compulsive symptoms induced by antipsychotics in schizophrenic bipolar disorder patients have been linked to EAAT3 (SLC1A1) gene variants. Post-mortem brain studies have shown that both classic and atypical antipsychotics reduce EAAT3, suggesting an involvement of this transporter in neuroleptic mechanisms beyond dopamine and serotonin modulation. Moreover, genetic variation in the human gene EAAT3 (SLC1A1) has been associated with antipsychotic drug response.

There is converging evidence from neurobiological data, human genetics, imaging studies and experimental treatments that EAAT3 is a key pathophysiological element in OCD and rigid-compulsive behavior in autism and in schizophrenia.

Curr. Opin. Pharmacol. 20, 116-123, 2015
J. Neurosci., 32, 2552-2563, 2012
J. Neurosci 29, 14581-14595, 2009
Arch. Gen. Psychiatry, 66, 408-416, 2009
Pharmacol. Ther. 107, 271-285, 2005
J. Neurochem. 98, 1007-1018, 2006
Nat. Neurosci., 9, 119-126, 2006

Objects of the present invention are the compounds of formula (I) and their aforementioned salts and esters and their use as therapeutically active substances, a process for the manufacture of the said compounds, intermediates, pharmaceutical compositions, medicaments containing the said compounds, their pharmaceutically acceptable salts or esters, the use of the said compounds, salts or esters for the treatment or prophylaxis of disorders or conditions that are associated with the activity of EAAT3, particularly in the treatment or prophylaxis of psychiatric disorders such as schizophrenia, bipolar disorder, obsessive-compulsive disorder or autism spectrum disorder, and the use of the said compounds, salts or esters for the production of medicaments for the treatment or prophylaxis of psychiatric disorders such as schizophrenia, bipolar disorder, obsessive-compulsive disorder or autism spectrum disorder.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, in particular hydrochloric acid, and organic acids such as acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition, these salts may be prepared by addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyimine resins and the like. Particular pharmaceutically acceptable salts of compounds of formula (I) are the hydrochloride salts, methanesulfonic acid salts and citric acid salts.

"Pharmaceutically acceptable esters" means that compounds of general formula (I) may be derivatised at functional groups to provide derivatives which are capable of conversion back to the parent compounds in vivo. Examples of such compounds include physiologically acceptable and metabolically labile ester derivatives, such as methoxymethyl esters, methylthiomethyl esters and pivaloyloxymethyl esters. Additionally, any physiologically acceptable equivalents of the compounds of general formula (I), similar to the metabolically labile esters, which are capable of producing the parent compounds of general formula (I) in vivo, are within the scope of this invention.

The term "protecting group" (PG) denotes a group which selectively blocks a reactive site in a multifunctional compound such that a chemical reaction can be carried out selectively at another unprotected reactive site in the meaning conventionally associated with it in synthetic chemistry. Protecting groups can be removed at the appropriate point. Exemplary protecting groups are amino-protecting groups, carboxy-protecting groups or hydroxy-protecting groups. Particular protecting groups are the tert-butoxycarbonyl (Boc), benzyloxycarbonyl (Cbz), fluorenylmethoxycarbonyl (Fmoc) and benzyl (Bn) groups. Further particular protecting groups are the tert-butoxycarbonyl (Boc) and the fluorenylmethoxycarbonyl (Fmoc) groups. More particular protecting group is the tert-butoxycarbonyl (Boc) group.

The abbreviation uM means microMolar and is equivalent to the symbol μM.

The abbreviation uL means microliter and is equivalent to the symbol μL.

The abbreviation ug means microgram and is equivalent to the symbol μg.

The compounds of formula (I) can contain several asymmetric centers and can be present in the form of optically pure enantiomers, mixtures of enantiomers such as, for example, racemates, optically pure diastereoisomers, mixtures of diastereoisomers, diastereoisomeric racemates or mixtures of diastereoisomeric racemates.

According to the Cahn-Ingold-Prelog Convention the asymmetric carbon atom can be of the "R" or "S" configuration.

Also an embodiment of the present invention are compounds according to formula (I) as described herein and pharmaceutically acceptable salts or esters thereof, in particular compounds according to formula (I) as described herein and pharmaceutically acceptable salts thereof, more particularly compounds according to formula (I) as described herein.

A particular embodiment of the present invention provides compounds according to formula (I) as described herein, wherein $R^1$ is methyl A particular embodiment of the present invention provides compounds according to formula (I) as described herein, wherein $R^2$ is selected from the group consisting of
  i) methyl,
  ii) ethyl, iii) isopropyl,
iv) tert-butyl,
v) cyclopropyl, and
vi) cyclopropylmethyl.

A particular embodiment of the present invention provides compounds according to formula (I) as described herein, wherein $R^3$ is selected from the group consisting of
i) hydrogen,
ii) chloro,
iii) fluoro,
iv) methyl
v) isopropyl,
vi) methoxy,
vii) cyano,
viii) cyclopropyl, and
ix) trifluoromethyl.

A further particular embodiment of the present invention provides compounds according to formula (I) as described herein, wherein $R^3$ is selected from the group consisting of
i) chloro,
ii) fluoro,
iii) cyano, and
iv) trifluoromethyl.

A particular embodiment of the present invention provides compounds according to formula (I) as described herein, wherein $R^4$ is H.

A more particular embodiment of the present invention provides compounds according to formula (I) as described herein, wherein
$R^{1'}$ and $R^1$ are both methyl;
$R^2$ is selected from the group consisting of
i) methyl,
ii) ethyl,
iii) isopropyl,
iv) tert-butyl,
v) cyclopropyl, and
vi) cyclopropylmethyl;
$R^3$ is selected from the group consisting of
i) hydrogen,
ii) chloro,
iii) fluoro,
iv) methyl
v) isopropyl,
vi) methoxy,
vii) cyano, and
viii) cyclopropyl
$R^4$ is selected from the group consisting of
i) hydrogen,
ii) chloro,
iii) fluoro, and
iv) methyl;
or pharmaceutically acceptable salts.

Particular examples of compounds of formula (I) as described herein are selected from
N-tert-butyl-3-(4-chlorophenyl)-5-(2-methylpyrazol-3-yl)benzamide;
N-tert-butyl-3-(2-tert-butylpyrazol-3-yl)-5-(4-fluorophenyl)benzamide;
N-tert-butyl-3-(2-tert-butylpyrazol-3-yl)-5-[4-(trifluoromethyl)phenyl]benzamide;
N-tert-butyl-3-(2-tert-butylpyrazol-3-yl)-5-(4-chlorophenyl)benzamide;
N-tert-butyl-3-(4-chlorophenyl)-5-(2-propan-2-ylpyrazol-3-yl)benzamide;
N-tert-butyl-3-(4-fluorophenyl)-5-(2-propan-2-ylpyrazol-3-yl)benzamide;
N-tert-butyl-3-(2-propan-2-ylpyrazol-3-yl)-5-[4-(trifluoromethyl)phenyl]benzamide;
N-tert-butyl-3-(3,4-difluorophenyl)-5-(2-propan-2-ylpyrazol-3-yl)benzamide;
N-tert-butyl-3-(4-methylphenyl)-5-(2-propan-2-ylpyrazol-3-yl)benzamide;
N-tert-butyl-3-(4-propan-2-ylphenyl)-5-(2-propan-2-ylpyrazol-3-yl)benzamide;
N-tert-butyl-3-(4-methoxyphenyl)-5-(2-propan-2-ylpyrazol-3-yl)benzamide;
N-tert-butyl-3-(3-chloro-4-fluorophenyl)-5-(2-propan-2-ylpyrazol-3-yl)benzamide;
N-tert-butyl-3-phenyl-5-(2-propan-2-ylpyrazol-3-yl)benzamide;
N-tert-butyl-3-(4-cyclopropylphenyl)-5-(2-propan-2-ylpyrazol-3-yl)benzamide;
N-tert-butyl-3-(4-fluoro-3-methylphenyl)-5-(2-propan-2-ylpyrazol-3-yl)benzamide;
N-tert-butyl-3-(4-chloro-3-fluorophenyl)-5-(2-propan-2-ylpyrazol-3-yl)benzamide;
N-tert-butyl-3-(4-cyanophenyl)-5-(2-propan-2-ylpyrazol-3-yl)benzamide;
3-(2-tert-butylpyrazol-3-yl)-5-(4-chlorophenyl)-N-(2-methylbutan-2-yl)benzamide;
3-(4-chlorophenyl)-N-(2-methylbutan-2-yl)-5-(2-propan-2-ylpyrazol-3-yl)benzamide;
N-tert-butyl-3-(3-fluoro-4-methylphenyl)-5-(2-propan-2-ylpyrazol-3-yl)benzamide;
3-(4-chlorophenyl)-N-(2-cyanopropan-2-yl)-5-(2-propan-2-ylpyrazol-3-yl)benzamide;
3-(2-tert-butylpyrazol-3-yl)-5-(4-chlorophenyl)-N-(2-cyanopropan-2-yl)benzamide;
N-tert-butyl-3-(2-cyclopropylpyrazol-3-yl)-5-(4-fluorophenyl)benzamide;
N-tert-butyl-3-(4-chlorophenyl)-5-(2-ethylpyrazol-3-yl)benzamide;
N-tert-butyl-3-(4-chlorophenyl)-5-[2-(cyclopropylmethyl)pyrazol-3-yl]benzamide;
3-(4-chlorophenyl)-N-(2-cyclopropylpropan-2-yl)-5-(2-propan-2-ylpyrazol-3-yl)benzamide;
N-tert-butyl-3-(2-tert-butylpyrazol-3-yl)-5-(4-fluoro-3-methylphenyl)benzamide;
N-tert-butyl-3-(2-tert-butylpyrazol-3-yl)-5-phenylbenzamide;
N-tert-butyl-3-(2-tert-butylpyrazol-3-yl)-5-(3-fluoro-4-methylphenyl)benzamide;
N-tert-butyl-3-(2-tert-butylpyrazol-3-yl)-5-(4-methylphenyl)benzamide;
N-tert-butyl-3-(2-tert-butylpyrazol-3-yl)-5-(4-methoxyphenyl)benzamide;
N-tert-butyl-3-(2-tert-butylpyrazol-3-yl)-5-(3-chloro-4-fluorophenyl)benzamide;
N-tert-butyl-3-(2-tert-butylpyrazol-3-yl)-5-(4-chloro-3-fluorophenyl)benzamide;
N-tert-butyl-3-(2-tert-butylpyrazol-3-yl)-5-(4-propan-2-ylphenyl)benzamide;
3-(2-tert-butylpyrazol-3-yl)-5-(4-chlorophenyl)-N-(2-cyclopropylpropan-2-yl)benzamide;
N-tert-butyl-3-(2-tert-butylpyrazol-3-yl)-5-(3,4-difluorophenyl)benzamide;
N-tert-butyl-3-(2-tert-butylpyrazol-3-yl)-5-(4-cyclopropylphenyl)benzamide;
N-tert-butyl-3-(2-tert-butylpyrazol-3-yl)-5-(4-cyanophenyl)benzamide;
3-(4-chlorophenyl)-N-(1-hydroxy-2-methylpropan-2-yl)-5-(2-propan-2-ylpyrazol-3-yl)benzamide;

3-(4-chlorophenyl)-5-(2-propan-2-ylpyrazol-3-yl)-N-(1,1,1-trifluoro-2-methylpropan-2-yl)benzamide;
3-(2-tert-butylpyrazol-3-yl)-5-(4-chlorophenyl)-N-(1-hydroxy-2-methylpropan-2-yl)benzamide;
3-(2-tert-butylpyrazol-3-yl)-5-(4-chlorophenyl)-N-(1,1,1-trifluoro-2-methylpropan-2-yl)benzamide;
N-tert-butyl-3-(2-cyclopropylpyrazol-3-yl)-5-[4-(trifluoromethyl)phenyl]benzamide;
N-tert-butyl-3-[2-(cyclopropylmethyl)pyrazol-3-yl]-5-[4-(trifluoromethyl)phenyl]benzamide;
N-tert-butyl-3-(4-chlorophenyl)-5-(2-cyclopropylpyrazol-3-yl)benzamide;
N-tert-butyl-3-[2-(cyclopropylmethyl)pyrazol-3-yl]-5-(4-fluorophenyl)benzamide;
N-tert-butyl-3-(2-ethylpyrazol-3-yl)-5-(4-fluorophenyl)benzamide;
N-tert-butyl-3-(2-ethylpyrazol-3-yl)-5-[4-(trifluoromethyl)phenyl]benzamide;
and pharmaceutically acceptable salts thereof.

Further particular examples of compounds of formula (I) as described herein are selected from
N-tert-butyl-3-(4-chlorophenyl)-5-(2-methylpyrazol-3-yl)benzamide;
N-tert-butyl-3-(2-tert-butylpyrazol-3-yl)-5-(4-fluorophenyl)benzamide;
N-tert-butyl-3-(4-chlorophenyl)-5-(2-propan-2-ylpyrazol-3-yl)benzamide;
N-tert-butyl-3-(4-fluorophenyl)-5-(2-propan-2-ylpyrazol-3-yl)benzamide;
N-tert-butyl-3-(2-propan-2-ylpyrazol-3-yl)-5-[4-(trifluoromethyl)phenyl]benzamide;
N-tert-butyl-3-(2-cyclopropylpyrazol-3-yl)-5-(4-fluorophenyl)benzamide;
N-tert-butyl-3-(4-chlorophenyl)-5-(2-ethylpyrazol-3-yl)benzamide;
N-tert-butyl-3-(4-chlorophenyl)-5-[2-(cyclopropylmethyl)pyrazol-3-yl]benzamide;
N-tert-butyl-3-(2-tert-butylpyrazol-3-yl)-5-(4-cyanophenyl)benzamide;
N-tert-butyl-3-(4-chlorophenyl)-5-(2-cyclopropylpyrazol-3-yl)benzamide;
N-tert-butyl-3-(2-ethylpyrazol-3-yl)-5-(4-fluorophenyl)benzamide;
and pharmaceutically acceptable salts thereof.

Processes for the manufacture of compounds of formula (I) as described herein are an object of the invention.

The preparation of compounds of formula (I) of the present invention may be carried out in sequential or convergent synthetic routes. Syntheses of the invention are shown in the following general schemes. The skills required for carrying out the reactions and purifications of the resulting products are known to those persons skilled in the art. In case a mixture of enantiomers or diastereoisomers is produced during a reaction, these enantiomers or diastereoisomers can be separated by methods described herein or known to the man skilled in the art such as e.g. (chiral) chromatography or crystallization. The substituents and indices used in the following description of the processes have the significance given herein.

In general the pyrazole derivatives I can either be prepared from the intermediate iodo derivatives II by coupling reaction with commercially available pyrazole boronic acids III.

or by coupling reaction of the iodo derivatives IV with commercially available boronic acid derivatives V.

The iodo derivatives II can be prepared starting from commercially available 3-iodo-5-nitrobenzoic acid VI.

Amide formation with the commercially available amines VII using standard conditions leads to the amides VIII which can coupled with commercially available boronic acid derivatives V to yield the nitro compounds IX which can be reduced with tin(II)chloride to yield the aniline derivatives X. Well known transformation of the aniline into iodine leads to the iodo building blocks II.

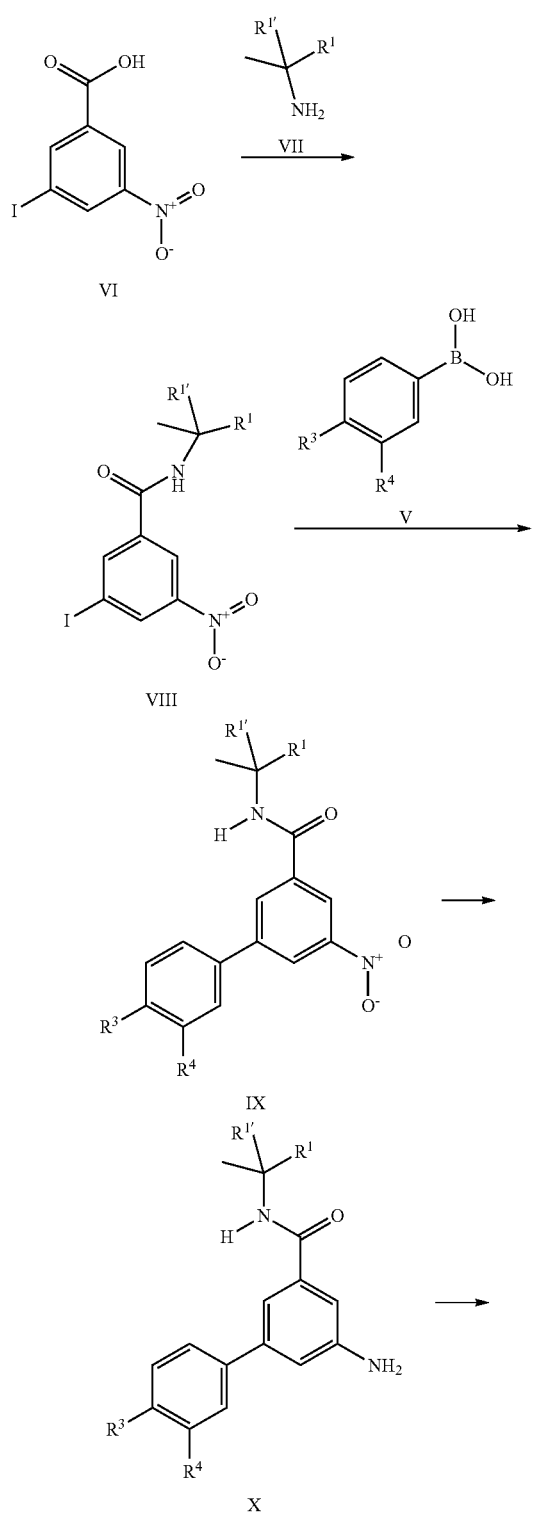

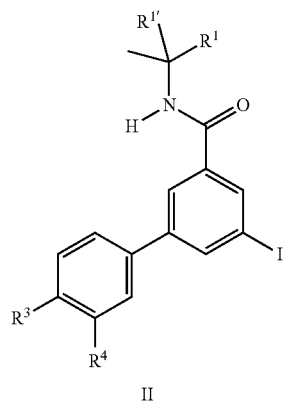

The synthesis of the iodo derivatives IV can start from the above described iodo derivatives VIII which can be transformed into the pyrazole derivatives XI by coupling reaction with commercially available pyrazole boronic acids III. Reduction of the nitro group to the aniline as described above leads to the derivatives XII. The iodo derivatives IV can be prepared from derivatives XII by known transformation of the aniline into the iodine.

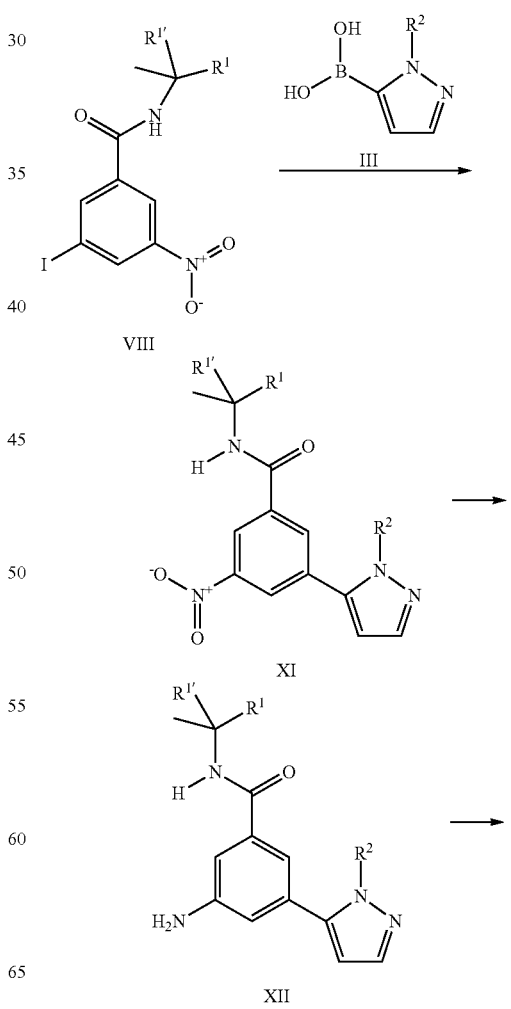

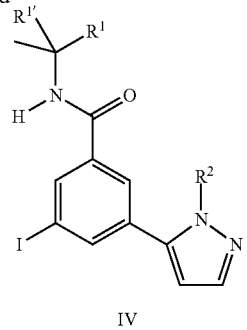

IV

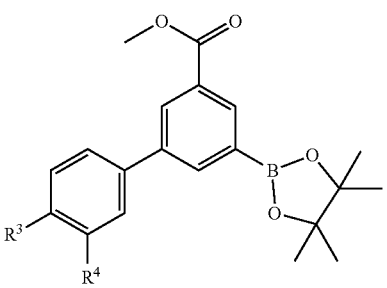

XV

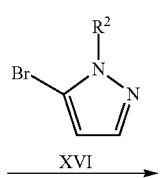

XVI

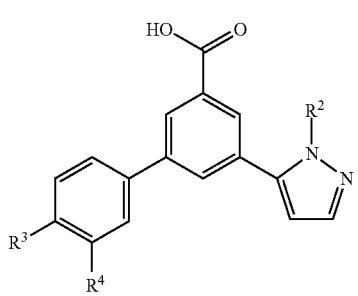

XVII

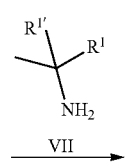

VII

An alternative route for the synthesis of the pyrazole derivatives I can start from the commercially available 3-iodo-5-nitrobenzoic acid VI. Coupling reaction with commercially available boronic acid derivatives V yields the nitro derivatives XII which can be transformed into the iodo derivatives XIV as described above by reduction of the nitro group followed by well-known transformation of the aniline into iodine, and subsequent ester formation. The iodo derivatives XIV can be transformed into the boronate derivatives XV by known methods. Coupling reaction with commercially available bromo pyrazole derivatives XVI, and subsequent ester hydrolysis by known methods yielded the acid derivatives XVII. Amide formation with the commercially available amines VII using standard conditions leads to the final amides I.

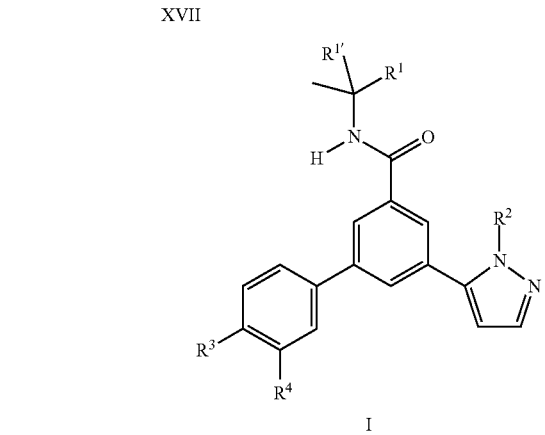

I

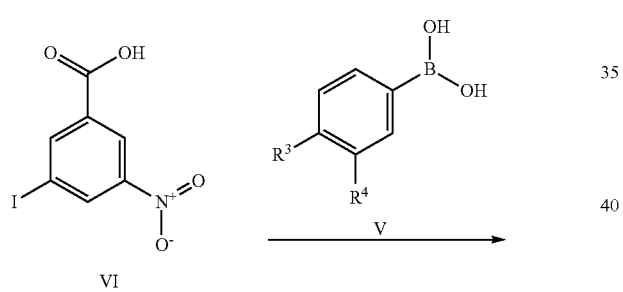

VI

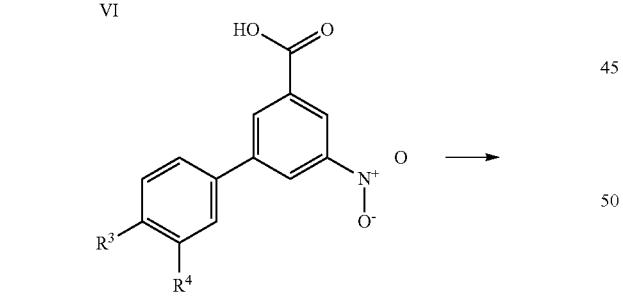

XIII

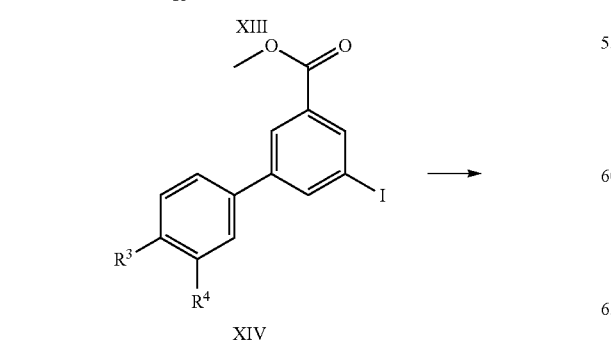

XIV

It is also possible to prepare the final compounds I by coupling reaction of the commercially available bromo pyrazole derivatives XVI with the boronates XVIII which can be prepared from the iodo building block II by known methods.

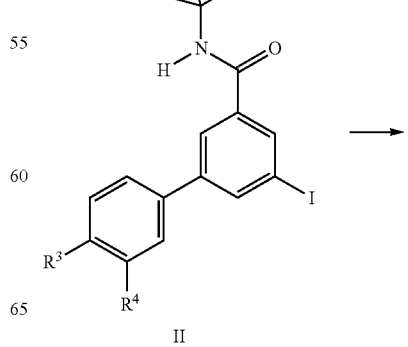

II

-continued

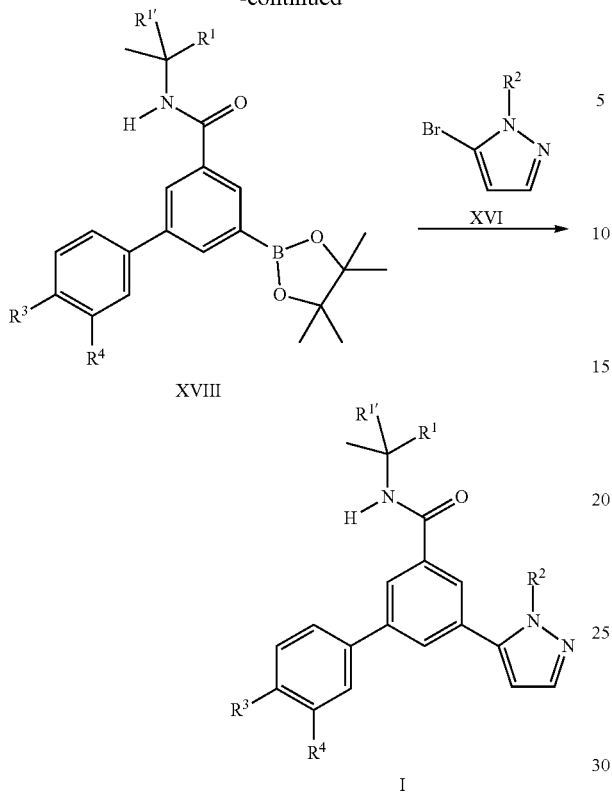

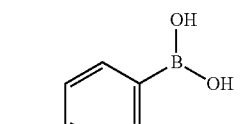

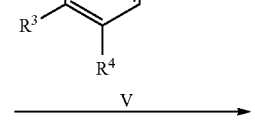

Also an embodiment of the present invention is a process to prepare a compound of formula (I) as defined above comprising a) the reaction of a compound of formula (II) in the presence of a compound of formula (III), wherein $R^1$, $R^{1'}$, $R^2$, $R^3$ and $R^4$ are as defined in any one of claim 1 to 9;

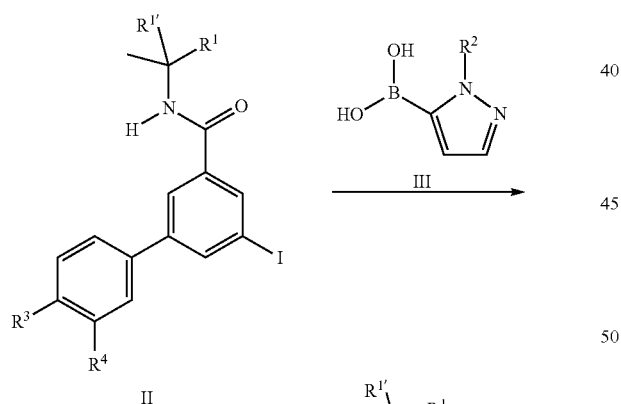

or b) the reaction of a compound of formula (IV) in the presence of a compound of formula (V), wherein $R^1$, $R^{1'}$, $R^2$, $R^3$ and $R^4$ are as defined herein;

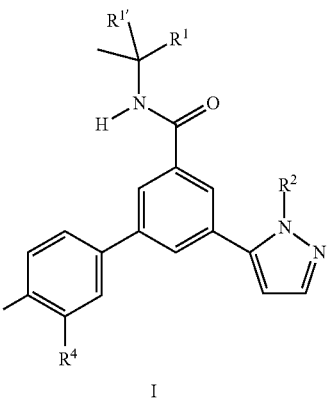

or c) the reaction of a compound of formula (XVII) in the presence of a compound of formula (VII), wherein $R^1$, $R^{1'}$, $R^2$, $R^3$ and $R^4$ are as defined in any one of claim 1 to 9;

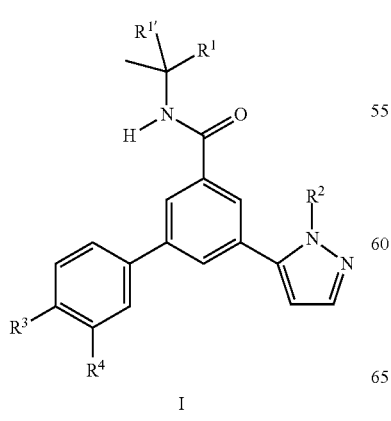

-continued

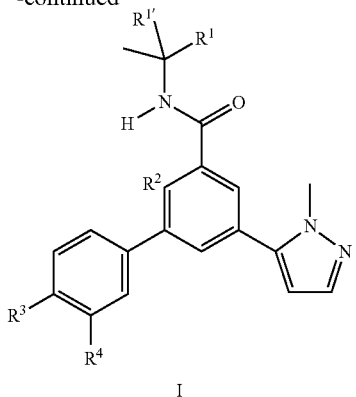

I or d) the reaction of a compound of formula (XVIII) in the presence of a compound of formula (XVI), wherein $R^1$, $R^{1'}$, $R^2$, $R^3$ and $R^4$ are as defined in any one of claim 1 to 9.

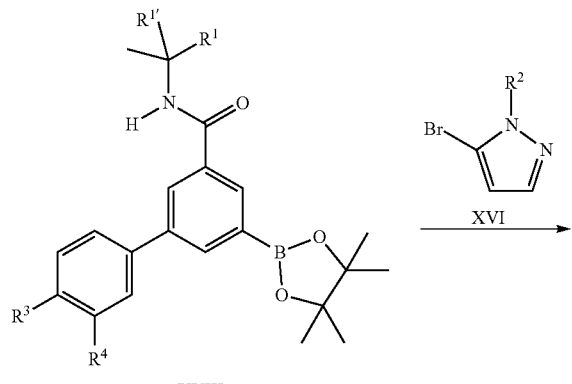

XVIII

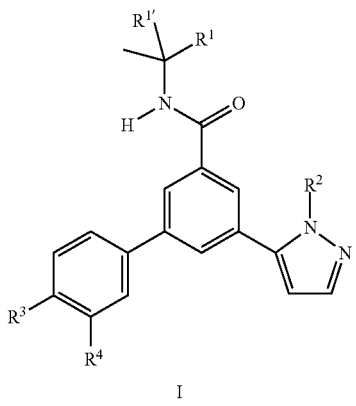

I

Also an object of the present invention is a compound according to formula (I) as described herein for use as a therapeutically active substance.

Likewise an object of the present invention is a pharmaceutical composition comprising a compound according to formula (I) as described herein and a therapeutically inert carrier.

A particular embodiment of the present invention is a compound according to formula (I) as described herein for the treatment or prophylaxis of ocular conditions, particularly glaucoma.

The present invention also relates to the use of a compound according to formula (I) as described herein for the preparation of a medicament for the treatment or prophylaxis of ocular conditions, particularly glaucoma.

Also an object of the invention is a method for the treatment or prophylaxis of ocular conditions, particularly glaucoma, which method comprises administering an effective amount of a compound according to formula (I) as described herein.

Also an embodiment of the present invention are compounds of formula (I) as described herein, when manufactured according to any one of the described processes.

Assay Procedures

The FLIPR Membrane Potential (FMP) Assay

HEK-293 cells stably expressing human EAAT3 were seeded at 55 000 cells/well in growth medium (DMEM glutamate free (Invitrogen 11960-044), 1% Pen Strep (10 ml/l GIBCO BRL N° 15140-023), 10% FCS non dialysed heat inactivated, 5 mg/l puromycin) in poly-D-lysine treated 96-well black microtiter plates with clear-bottom. After 24 h, the growth medium was removed and 100 μl/well of Krebs buffer (140 mM NaCl, 4.7 mM KCl, 2.5 mM $CaCl_2$, 1.2 mM $MgCl_2$, 11 mM HEPES, 10 mM D-glucose, pH=7.4) added. The cells were then loaded by adding 100 μl/well FMP assay dye (FLIPR Membrane Potential assay reagent, Molecular Devices). The 96-well plates were then incubated at 37° C. for 1 h. The depolarization of the cells will cause more dye to enter in the cells, where it will bind to intracellular proteins and lipids and cause an increase in the fluorescence signal. Antagonist potency at human EAAT3 was determined by using L-glutamate as agonist at a concentration which gives 80% of the maximum response. The antagonists were applied 15 min before the application of the agonist L-glutamate. The assays were performed at room temperature and measurements done by using a Fluorometric Imaging Plate Reader (FLIPR, Molecular Devices) and filter #2. Responses were measured as peak increase in fluorescence minus basal (i.e. fluorescence without addition of L-glutamate). Kb was determined using the Cheng-Prusoff equation $Kb=IC_{50}/[1+(A/EC_{50})]$, where $IC_{50}$ is the concentration of the antagonist producing 50% inhibition, A is the concentration of the agonist against which the $IC_{50}$ is being determined (at $EC_{50}$) and $EC_{50}$ is the concentration of the agonist producing 50% inhibition.

| Example | EAAT3 Kb (μM) |
| --- | --- |
| 1 | 0.24 |
| 2 | 0.19 |
| 3 | 0.28 |
| 4 | 0.32 |
| 5 | 0.17 |
| 6 | 0.095 |
| 7 | 0.18 |
| 8 | 0.39 |
| 9 | 0.26 |
| 10 | 0.55 |
| 11 | 0.29 |
| 12 | 0.61 |
| 13 | 0.3 |
| 14 | 0.88 |
| 15 | 1.28 |
| 16 | 0.31 |
| 17 | 0.33 |
| 18 | 3.42 |
| 19 | 0.89 |
| 20 | 0.36 |
| 21 | 0.32 |
| 22 | 0.37 |

-continued

| Example | EAAT3 Kb (μM) |
|---|---|
| 23 | 0.11 |
| 24 | 0.17 |
| 25 | 0.25 |
| 26 | 1.52 |
| 27 | 0.93 |
| 28 | 0.47 |
| 29 | 0.39 |
| 30 | 0.37 |
| 31 | 0.25 |
| 32 | 0.41 |
| 33 | 0.29 |
| 34 | 0.6 |
| 35 | 0.92 |
| 36 | 0.44 |
| 37 | 1.13 |
| 38 | 0.24 |
| 39 | 0.27 |
| 40 | 0.62 |
| 41 | 0.26 |
| 42 | 0.89 |
| 43 | 0.32 |
| 44 | 0.4 |
| 45 | 0.26 |
| 46 | 0.28 |
| 47 | 0.11 |
| 48 | 0.29 |

The compounds of formula (I) and their pharmaceutically acceptable salts can be used as medicaments (e.g. in the form of pharmaceutical preparations). The pharmaceutical preparations can be administered internally, such as orally (e.g. in the form of tablets, coated tablets, dragées, hard and soft gelatin capsules, solutions, emulsions or suspensions), nasally (e.g. in the form of nasal sprays), rectally (e.g. in the form of suppositories) or topical ocularly (e.g. in the form of solutions, ointments, gels or water soluble polymeric inserts). However, the administration can also be effected parenterally, such as intramuscularly, intravenously, or intraocularly (e.g. in the form of sterile injection solutions).

The compounds of formula (I) and their pharmaceutically acceptable salts can be processed with pharmaceutically inert, inorganic or organic adjuvants for the production of tablets, coated tablets, dragées, hard gelatin capsules, injection solutions or topical formulations Lactose, corn starch or derivatives thereof, talc, stearic acid or its salts etc. can be used, for example, as such adjuvants for tablets, dragées and hard gelatin capsules.

Suitable adjuvants for soft gelatin capsules, are, for example, vegetable oils, waxes, fats, semi-solid substances and liquid polyols, etc.

Suitable adjuvants for the production of solutions and syrups are, for example, water, polyols, saccharose, invert sugar, glucose, etc.

Suitable adjuvants for injection solutions are, for example, water, alcohols, polyols, glycerol, vegetable oils, etc.

Suitable adjuvants for suppositories are, for example, natural or hardened oils, waxes, fats, semi-solid or liquid polyols, etc.

Suitable adjuvants for topical ocular formulations are, for example, cyclodextrins, mannitol or many other carriers and excipients known in the art.

Moreover, the pharmaceutical preparations can contain preservatives, solubilizers, viscosity-increasing substances, stabilizers, wetting agents, emulsifiers, sweeteners, colorants, flavorants, salts for varying the osmotic pressure, buffers, masking agents or antioxidants. They can also contain still other therapeutically valuable substances.

The dosage can vary in wide limits and will, of course, be fitted to the individual requirements in each particular case. In general, in the case of oral administration a daily dosage of about 0.1 mg to 20 mg per kg body weight, preferably about 0.5 mg to 4 mg per kg body weight (e.g. about 300 mg per person), divided into preferably 1-3 individual doses, which can consist, for example, of the same amounts, should it be appropriate. In the case of topical administration, the formulation can contain 0.001% to 15% by weight of medicament and the required dose, which can be between 0.1 and 25 mg in can be administered either by single dose per day or per week, or by multiple doses (2 to 4) per day, or by multiple doses per week It will, however, be clear that the upper or lower limit given herein can be exceeded when this is shown to be indicated.

Preparation of Pharmaceutical Compositions Comprising Compounds of the Invention:

Tablets of the following composition are manufactured in the usual manner:

| | mg/tablet | | | |
|---|---|---|---|---|
| ingredient | 5 | 25 | 100 | 500 |
| Compound of formula I | 5 | 25 | 100 | 500 |
| Lactose Anhydrous DTG | 125 | 105 | 30 | 150 |
| Sta-Rx 1500 | 6 | 6 | 6 | 60 |
| Microcrystalline Cellulose | 30 | 30 | 30 | 450 |
| Magnesium Stearate | 1 | 1 | 1 | 1 |
| Total | 167 | 167 | 167 | 831 |

Manufacturing Procedure
1. Mix ingredients 1, 2, 3 and 4 and granulate with purified water.
2. Dry the granules at 50° C.
3. Pass the granules through suitable milling equipment.
4. Add ingredient 5 and mix for three minutes; compress on a suitable press.

Capsules of the Following Composition are Manufactured:

| | mg/capsule | | | |
|---|---|---|---|---|
| ingredient | 5 | 25 | 100 | 500 |
| Compound of formula I | 5 | 25 | 100 | 500 |
| Hydrous Lactose | 159 | 123 | 148 | — |
| Corn Starch | 25 | 35 | 40 | 70 |
| Talk | 10 | 15 | 10 | 25 |
| Magnesium Stearate | 1 | 2 | 2 | 5 |
| Total | 200 | 200 | 300 | 600 |

Manufacturing Procedure
1. Mix ingredients 1, 2 and 3 in a suitable mixer for 30 minutes.
2. Add ingredients 4 and 5 and mix for 3 minutes.
3. Fill into a suitable capsule.

A compound of formula I lactose and corn starch are firstly mixed in a mixer and then in a comminuting machine. The mixture is returned to the mixer; the talc is added thereto and mixed thoroughly. The mixture is filled by machine into suitable capsules, e.g. hard gelatin capsules.

Injection Solutions of the Following Composition are Manufactured:

| ingredient | mg/injection solution. |
|---|---|
| Compound of formula I | 3 |
| Polyethylene Glycol 400 | 150 |
| acetic acid | q.s. ad pH 5.0 |
| water for injection solutions | ad 1.0 ml |

The invention is illustrated hereinafter by Examples, which have no limiting character.

In case the preparative examples are obtained as a mixture of enantiomers, the pure enantiomers can be obtained by methods described herein or by methods known to those skilled in the art, such as e.g. chiral chromatography or crystallization.

EXAMPLES

Intermediate 1:
N-tert-Butyl-3-(4-chlorophenyl)-5-iodobenzamide

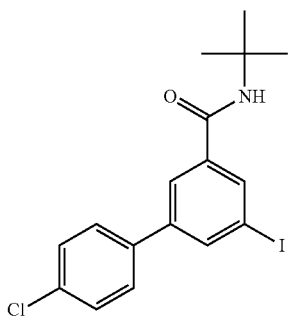 [SMILES: CC(C)(C)NC(=O)c1cc(I)cc(-c2ccc(Cl)cc2)c1]

Step A

To a stirred solution of commercially available 3-iodo-5-nitrobenzoic acid (2 g, 6.83 mmol) in THF (49.1 ml) was added at room temperature N,N-diisopropylethylamine (2.21 g, 2.98 ml, 17.1 mmol), 2-methylpropan-2-amine (611 mg, 878 μl, 8.19 mmol) and O-(benzotriazol-1-yl)-N,N,N', N'-tetramethyluronium tetrafluoroborate (TBTU) (3.51 g, 10.9 mmol). The reaction mixture was stirred at room temperature for 4 h, evaporated and the residue purified by flash chromatography on silica gel [heptane/ethyl acetate (0-50%)] to yield N-tert-butyl-3-iodo-5-nitrobenzamide (2.31 g, 97%) as an off-white solid, MS (ISP) m/z=349.0 [(M+H)+], mp 166° C.

Step B

A mixture of N-tert-butyl-3-iodo-5-nitrobenzamide (2.3 g, 6.61 mmol) and (4-chlorophenyl)boronic acid (1.34 g, 8.59 mmol) in 1,2-dimethoxyethane (44 ml) and 2M Na₂CO₃ (11 ml, 22 mmol) was purged with argon in an ultrasonic bath for 5 min, triphenylphosphine (347 mg, 1.32 mmol) and palladium(II)acetate (148 mg, 661 μmol) were added and the reaction mixture was stirred for 3 h under reflux conditions. The reaction mixture poured into water (50 ml) and extracted with ethylacetate (2×50 ml). The combined organic layers were washed with brine (40 ml), dried (MgSO₄) and evaporated to give the crude product (3.09 g) as brown solid, which was purified by flash chromatography on silica gel [heptane/ethyl acetate (0-50%)] to yield N-tert-butyl-3-(4-chlorophenyl)-5-nitrobenzamide (2.38 g, 92%) as a brown solid, MS (ISP) m/z=333.1 [(M+H)+], mp 186° C.

Step C

To a stirred solution of N-tert-butyl-3-(4-chlorophenyl)-5-nitrobenzamide (2.38 g, 6.58 mmol) in MeOH (49.8 ml) was added at room temperature tin(II)chloride dihydrate (5.94 g, 26.3 mmol) and the reaction mixture was stirred under reflux conditions for 2 h, evaporated, water (50 ml) and 2N NaOH (50 ml) were added and the mixture was extracted with ethyl acetate (2×75 ml). The combined organic layers were washed with water (50 ml) and brine (50 ml), dried (MgSO₄) and evaporated. The crude product (brown solid, 2.08 g) was purified by flash chromatography on silica gel [dichloromethane/MeOH (1-5%)] to yield 3-amino-N-tert-butyl-5-(4-chlorophenyl)-benzamide (1.90 g, 95%) as a light brown solid, MS (ISP) m/z=303.1 [(M+H)+], mp 231° C.

Step D

A mixture of 3-amino-N-tert-butyl-5-(4-chlorophenyl)-benzamide (1.899 g, 6.27 mmol), isoamyl nitrite (4.59 g, 5.27 ml, 37.6 mmol) and diiodomethane (10.2 g, 3.07 ml, 37.6 mmol) was stirred at room temperature for 1 h, and afterwards at 65° C. for 5 h. The reaction mixture was cooled to room temperature, toluene (30 ml) was added and the mixture was evaporated to dryness which was repeated 3 times. The residue was purified by flash chromatography on silica gel [heptane/ethy acetate (0-40%)] to yield the title compound (1.41 g, 55%) as light yellow foam, MS (ISP) m/z=414.0 [(M+H)+].

Intermediate 2:
N-tert-Butyl-3-(4-fluorophenyl)-5-iodobenzamide

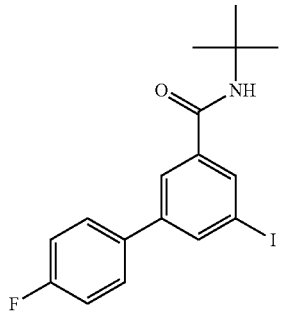 [SMILES: CC(C)(C)NC(=O)c1cc(I)cc(-c2ccc(F)cc2)c1]

Step A 3-(4-Fluorophenyl)-5-nitrobenzoic acid, light brown solid (4.33 g, 97%), MS (ISN) m/z=260.1 [(M−H)−], mp 182° C., was prepared in accordance with the general method of intermediate 1, step B, from commercially available 3-iodo-5-nitrobenzoic acid (5.0 g, 17.1 mmol) and commercially available (4-fluorophenyl)-boronic acid (2.63 g, 18.8 mmol).

Step B

N-tert-Butyl-3-(4-fluorophenyl)-5-nitrobenzamide, yellow solid (1.03 g, 93%), MS (ISP) m/z=317.1 [(M+H)+], mp 180° C., was prepared in accordance with the general method of intermediate 1, step A, from 3-(4-fluorophenyl)-5-nitrobenzoic acid (914 mg, 3.50 mmol) and commercially available 2-methylpropan-2-amine (307 mg, 441 μl, 4.20 mmol).

Step C

3-Amino-N-tert-butyl-5-(4-fluorophenyl)-benzamide, light yellow solid (0.93 g, 99%), MS (ISP) m/z=287.2 [(M+H)+], mp 215° C., was prepared in accordance with the general method of intermediate 1, step C, from N-tert-Butyl-3-(4-fluorophenyl)-5-nitrobenzamide (1.03 g, 3.26 mmol).

Step D

The title compound, off-white (0.83 g, 64%), MS (ISP) m/z=398.1 [(M+H)+], mp 146° C., was prepared in accordance with the general method of intermediate 1, step D, from 3-amino-N-tert-butyl-5-(4-fluorophenyl)-benzamide (0.93 g, 3.25 mmol).

Intermediate 3: N-tert-Butyl-3-iodo-5-[4-(trifluoromethyl)-phenyl]-benzamide

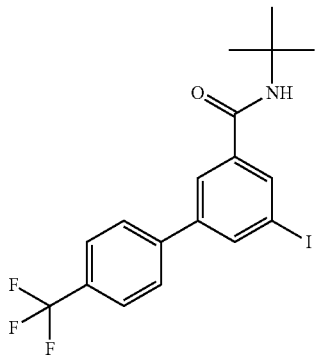 [SMILES: CC(C)(C)NC(=O)c1cc(I)cc(-c2ccc(C(F)(F)F)cc2)c1]

Step A

N-tert-Butyl-3-nitro-5-[4-(trifluoromethyl)-phenyl]-benzamide, light brown solid (0.52 g, 99%), MS (ISP) m/z=367.2 [(M+H)+], mp 187.5° C., was prepared in accordance with the general method of intermediate 1, step B, from N-tert-butyl-3-iodo-5-nitrobenzamide (intermediate 1, step A) (0.50 g, 1.44 mmol) and commercially available (4-trifluoromethyl-phenyl)-boronic acid (355 mg, 1.87 mmol).

Step B

3-Amino-N-tert-butyl-5-[4-(trifluoromethyl)-phenyl]-benzamide, light yellow solid (0.48 g, 99%), MS (ISP) m/z=337.2 [(M+H)+], mp 228.5° C., was prepared in accordance with the general method of intermediate 1, step C, from N-tert-butyl-3-nitro-5-[4-(trifluoromethyl)-phenyl]-benzamide (0.52 g, 1.42 mmol).

Step C

The title compound, light yellow solid (0.44 g, 72%), MS (ISP) m/z=448.1 [(M+H)+], mp 139° C., was prepared in accordance with the general method of intermediate 1, step D, from 3-amino-N-tert-butyl-5-[4-(trifluoromethyl)-phenyl]-benzamide (0.46 g, 1.37 mmol).

Intermediate 4: N-tert-Butyl-3-iodo-5-(2-propan-2-yl-pyrazol-3-yl)-benzamide

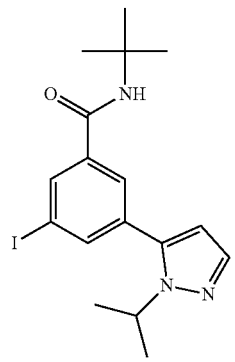 [SMILES: CC(C)n1nccc1-c1cc(I)cc(C(=O)NC(C)(C)C)c1]

Step A

N-tert-Butyl-3-nitro-5-(2-propan-2-yl-pyrazol-3-yl)-benzamide, off-white solid (1.29 g, 78%), MS (ISP) m/z=331.2 [(M+H)+], mp 156° C., was prepared in accordance with the general method of intermediate 1, step B, from N-tert-butyl-3-iodo-5-nitrobenzamide (intermediate 1, step A) (1.74 g, 5.0 mmol) and commercially available (1-isopropyl-1H-pyrazol-5-yl)-boronic acid (1.0 g, 6.5 mmol).

Step B

3-Amino-N-tert-butyl-5-(2-propan-2-yl-pyrazol-3-yl)-benzamide, white solid (1.15 g, 98%), MS (ISP) m/z=301.2 [(M+H)+], mp 195° C., was prepared in accordance with the general method of intermediate 1, step C, from N-tert-butyl-3-nitro-5-(2-propan-2-yl-pyrazol-3-yl)-benzamide (1.29 g, 3.90 mmol).

Step C

The title compound, light yellow foam (1.23 g, 78%), MS (ISP) m/z=412.2 [(M+H)+], mp 166° C., was prepared in accordance with the general method of intermediate 1, step D, from 3-amino-N-tert-butyl-5-(2-propan-2-yl-pyrazol-3-yl)-benzamide (1.15 g, 3.83 mmol).

Intermediate 5: 3-(4-Chlorophenyl)-5-iodo-N-(2-methylbutan-2-yl)-benzamide

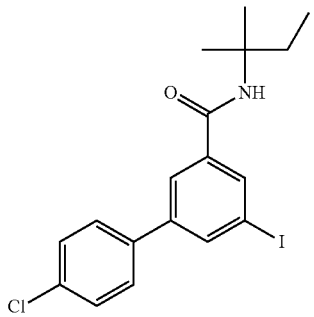 [SMILES: CCC(C)(C)NC(=O)c1cc(I)cc(-c2ccc(Cl)cc2)c1]

Step A

3-Iodo-N-(2-methylbutan-2-yl)-5-nitrobenzamide, off-white solid (1.44 g, 99%), MS (ISP) m/z=363.0 [(M+H)+], mp 117° C., was prepared in accordance with the general method of intermediate 1, step A, from commercially available 3-iodo-5-nitrobenzoic acid (1.17 g, 4.0 mmol) and commercially available 2-methylbutan-2-amine (0.42 g, 4.8 mmol).

Step B 3-(4-Chlorophenyl)-N-(2-methylbutan-2-yl)-5-nitrobenzamide, light brown solid (0.69 g, 99%), MS (ISP) m/z=347.1 [(M+H)+], mp 171.5° C., was prepared in accordance with the general method of intermediate 1, step B, from 3-iodo-N-(2-methylbutan-2-yl)-5-nitrobenzamide (0.72 g, 1.99 mmol) and commercially available (4-chlorophenyl)-boronic acid (405 mg, 2.59 mmol).

Step C

3-Amino-5-(4-chlorophenyl)-N-(2-methylbutan-2-yl)-benzamide, light yellow solid (0.62 g, 97%), MS (ISP) m/z=317.2 [(M+H)+], mp 192° C., was prepared in accordance with the general method of intermediate 1, step C, from 3-(4-chlorophenyl)-N-(2-methylbutan-2-yl)-5-nitrobenzamide (1.25 g, 3.48 mmol).

Step D

The title compound, light yellow solid (0.65 g, 78%), MS (ISP) m/z=428.1 [(M+H)+], mp 136° C., was prepared in accordance with the general method of intermediate 1, step D, from 3-amino-5-(4-chlorophenyl)-N-(2-methylbutan-2-yl)-benzamide (0.62 g, 1.96 mmol).

Intermediate 6: 3-(4-Chlorophenyl)-N-(2-cyanopropan-2-yl)-5-iodo-benzamide

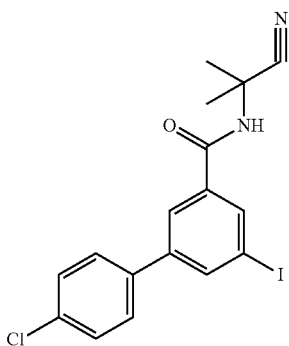 [SMILES: CC(C)(C#N)NC(=O)c1cc(I)cc(-c2ccc(Cl)cc2)c1]

Step A

To a stirred solution of commercially available 3-iodo-5-nitrobenzoic acid (3.60 g, 12.3 mmol) and Pd(Ph3P)4 (454 mg, 393 µmol) in toluene (68 ml) and ethanol (11.3 ml) was added at room temperature commercially available 4-chloro-phenylboronic acid (2.11 g, 13.5 mmol) and a solution of Cs2CO3 (4.40 g, 13.5 mmol) in water (4.56 ml). The reaction mixture was stirred under reflux conditions for 18 h and then cooled to room temperature. To the mixture was added 2N NaOH (50 ml), and the reaction mixture was stirred for 30 min at room temperature. Some precipitated material was collected by filtration. The organic layer was separated, and to the water layer together with the precipitated material was added conc. hydrochloric acid (18 ml) to reach pH<4. The mixture was extracted with ethyl acetate (2×75 ml), the combined organic layers were washed with brine, dried (MgSO4) and evaporated to yield crude 3-(4-chlorophenyl)-5-nitrobenzoic acid (3.26 g, 11.7 mmol) as brown solid, MS (ISN) m/z=276.1 [(M–H)−], which was subsequently dissolved in methanol (29 ml). To the stirred solution was added dropwise thionyl chloride (1.54 g, 0.94 ml, 12.9 mmol) at 0° C. The reaction mixture was allowed to warm to room temperature, and was afterwards stirred under reflux conditions for 2 h. The solvent was removed in vacuo to yield crude methyl 3-(4-chlorophenyl)-5-nitrobenzoate (3.26 g, 11.2 mmol) as a brown solid, MS (ISP) m/z=292.1 [(M+H)+], which was subsequently dissolved in methanol (29 ml). To the stirred solution was added at room temperature tin(II)chloride (8.48 g, 44.7 mmol), the reaction mixture was stirred under reflux conditions for 3 h, evaporated, the residue was dissolved in water (150 ml) and basified to pH=9 by addition of Na2CO3. The mixture was extracted with dichloro-methane (3×75 ml), the combined organic layers were washed with water (150 ml), brine (150 ml), dried (MgSO4) and evaporated. The crude product was purified by flash chromatography on silica gel [heptane/ethyl acetate (20-50%)] to yield methyl 3-amino-5-(4-chlorophenyl)-benzoate (2.29 g, 71%) as a yellow solid, MS (ISP) m/z=262.1 [(M+H)+], mp 120° C.

Step B

A suspension of methyl 3-amino-5-(4-chlorophenyl)-benzoate (2.45 g, 9.36 mmol), isoamyl nitrite (6.85 g, 7.86 ml, 56.2 mmol), copper(I)iodide (1.78 g, 9.36 mmol) and diiodomethane (15.2 g, 4.58 ml, 56.2 mmol) in THF (24.1 ml) was allowed to stir at room temperature for 1 h hour and afterwards under reflux conditions for 3 h. To the reaction mixture was added toluene (30 ml) at room temperature, the mixture was evaporated and purified by flash chromatography on silica gel [heptane/ethyl acetate (0-50%)] to yield methyl 5-(4-chlorophenyl)-3-iodo-benzoate (3.17 g, 91%) as a light yellow solid, MS (ISP) m/z=372.1 [(M+H)+], mp 90.5° C.

Step C

To a stirred mixture of methyl 5-(4-chlorophenyl)-3-iodo-benzoate (499 mg, 1.34 mmol) in THF (2.24 ml), methanol (2.24 ml) and water (2.24 ml) was added at room temperature lithium hydroxide monohydrate (73.1 mg, 1.74 mmol). The reaction mixture was allowed to stir for 4 h at room temperature, concentrated to one third, 2N HCl solution (2.58 ml) was added, the precipitate collected by filtration and dried to yield 5-(4-chlorophenyl)-3-iodo-benzoic acid (440 mg, 92%) as an off-white solid, MS (ISN) m/z=357.1 [(M–H)−], mp 222.5° C.

Step D

The title compound, light yellow oil (0.51 g, 98%), MS (ISP) m/z=425.2 [(M+H)+], was prepared in accordance with the general method of intermediate 1, step A, from 5-(4-chlorophenyl)-3-iodo-benzoic acid (441 mg, 1.23 mmol) and commercially available 2-amino-2-methyl-propanenitrile (155 mg, 169 µl, 1.84 mmol).

Intermediate 7: N-tert-Butyl-3-(2-tert-butyl-pyrazol-3-yl)-5-iodo-benzamide

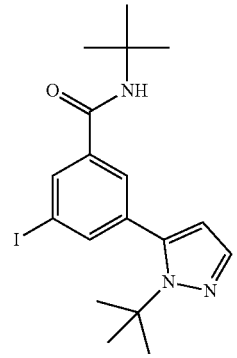 [SMILES: CC(C)(C)NC(=O)c1cc(I)cc(-c2ccnn2C(C)(C)C)c1]

Step A

N-tert-Butyl-3-(2-tert-butylpyrazol-3-yl)-5-nitrobenzamide, yellow solid (1.56 g, 81%), MS (ISP) m/z=345.2 [(M+H)$^+$], mp 179.5° C., was prepared in accordance with the general method of intermediate 1, step B, from N-tert-butyl-3-iodo-5-nitrobenzamide (intermediate 1, step A) (1.95 g, 5.6 mmol) and commercially available 1-(tert-butyl)-5-(4,4,5,5-tetramethyl-1,3,2-dioxaborolan-2-yl)-1H-pyrazole (1.82 g, 7.28 mmol)

Step B

3-Amino-N-tert-butyl-5-(2-tert-butyl-pyrazol-3-yl)-benzamide, off-white solid (1.41 g, 100%), MS (ISP) m/z=315.2 [(M+H)$^+$], mp 219.5° C., was prepared in accordance with the general method of intermediate 1, step C, from N-tert-butyl-3-(2-tert-butylpyrazol-3-yl)-5-nitrobenzamide (1.54 g, 4.47 mmol).

Step C

The title compound, off-white solid (1.28 g, 67%), MS (ISP) m/z=426.2 [(M+H)$^+$], mp 206° C., was prepared in accordance with the general method of intermediate 1, step D, from 3-amino-N-tert-butyl-5-(2-tert-butyl-pyrazol-3-yl)-benzamide (1.42 g, 4.52 mmol).

Intermediate 8: 3-(4-Chlorophenyl)-N-(2-cyclopropylpropan-2-yl)-5-iodobenzamide

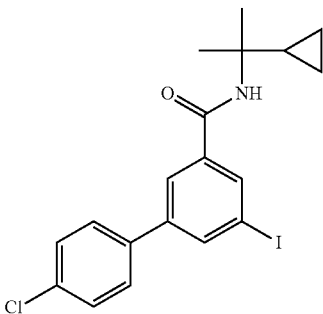 [SMILES: CC(C)(NC(=O)c1cc(I)cc(-c2ccc(Cl)cc2)c1)C1CC1]

Step A 3-(4-Chlorophenyl)-N-(2-cyclopropylpropan-2-yl)-5-nitrobenzamide, light yellow solid (1.25 g, 92%), MS (ISP) m/z=359.1 [(M+H)$^+$], mp 172° C., was prepared in accordance with the general method of intermediate 1, step A, from 3-(4-chlorophenyl)-5-nitrobenzoic acid (intermediate 2, step A) (1.05 g, 3.78 mmol) and commercially available 2-cyclopropylpropan-2-amine (0.45 g, 4.54 mmol).

Step B

3-Amino-5-(4-chlorophenyl)-N-(2-cyclopropylpropan-2-yl)-benzamide, light yellow solid (0.98 g, 85%), MS (ISP) m/z=329.1 [(M+H)$^+$], mp 199° C., was prepared in accordance with the general method of intermediate 1, step C, from 3-(4-chlorophenyl)-N-(2-cyclopropyl-propan-2-yl)-5-nitrobenzamide (1.25 g, 3.48 mmol).

Step C

The title compound, light brown solid (1.0 g, 77%), MS (ISP) m/z=440.1 [(M+H)$^+$], mp 152° C., was prepared in accordance with the general method of intermediate 1, step D, from 3-amino-5-(4-chlorophenyl)-N-(2-cyclopropylpropan-2-yl)-benzamide (0.97 g, 2.95 mmol).

Intermediate 9: 3-(4-Chlorophenyl)-N-(1-hydroxy-2-methylpropan-2-yl)-5-iodo-benzamide

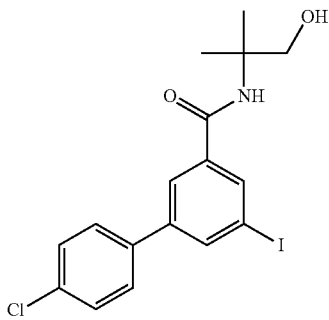 [SMILES: CC(C)(CO)NC(=O)c1cc(I)cc(-c2ccc(Cl)cc2)c1]

Step A 3-(4-Chlorophenyl)-N-(1-hydroxy-2-methylpropan-2-yl)-5-nitrobenzamide, light yellow foam (1.36 g, 72%), MS (ISP) m/z=349.1 [(M+H)$^+$], was prepared in accordance with the general method of intermediate 1, step A, from 3-(4-chlorophenyl)-5-nitrobenzoic acid (intermediate 2, step A) (1.50 g, 5.40 mmol) and commercially available 2-amino-2-methylpropan-1-ol (0.58 g, 6.48 mmol).

Step B

3-Amino-5-(4-chlorophenyl)-N-(1-hydroxy-2-methyl-propan-2-yl)-benzamide, light yellow foam (0.54 g, 99%), MS (ISP) m/z=319.2 [(M+H)$^+$], mp 150° C., was prepared in accordance with the general method of intermediate 1, step C, from 3-(4-chlorophenyl)-N-(1-hydroxy-2-methyl-propan-2-yl)-5-nitrobenzamide (0.60 g, 1.72 mmol).

Step C

The title compound, light yellow foam (0.52 g, 74%), MS (ISP) m/z=430.1 [(M+H)$^+$], mp 79° C., was prepared in accordance with the general method of intermediate 1, step D, from 3-amino-5-(4-chlorophenyl)-N-(1-hydroxy-2-methylpropan-2-yl)-benzamide (0.52 g, 1.63 mmol).

Intermediate 10: 3-(4-Chlorophenyl)-5-iodo-N-(1,1,1-trifluoro-2-methyl-propan-2-yl)-benzamide

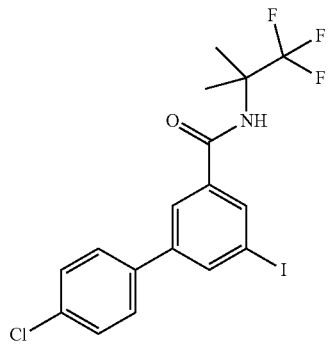 [SMILES: CC(C)(NC(=O)c1cc(I)cc(-c2ccc(Cl)cc2)c1)C(F)(F)F]

Step A 3-(4-Chlorophenyl)-5-nitro-N-(1,1,1-trifluoro-2-methyl-propan-2-yl)-benzamide, off-white solid (0.63 g, 43%), MS (ISP) m/z=387.1 [(M+H)$^+$], mp 180° C., was prepared in accordance with the general method of intermediate 1, step A, from 3-(4-chlorophenyl)-5-nitrobenzoic acid (intermediate 2, stepA) (1.05 g, 3.78 mmol) and commercially available 1,1,1-trifluoro-2-methylpropan-2-amine (577 mg, 4.54 mmol).

Step B

3-Amino-5-(4-chlorophenyl)-N-(1,1,1-trifluoro-2-methylpropan-2-yl)-benzamide, light yellow solid (0.57 g, 98%), MS (ISP) m/z=357.1 [(M+H)$^+$], mp 150° C., was prepared in accordance with the general method of intermediate 1, step C, from 3-(4-chlorophenyl)-5-nitro-N-(1,1,1-trifluoro-2-methylpropan-2-yl)-benzamide (0.63 g, 1.63 mmol).

Step C

The title compound, light yellow solid (0.53 g, 71%), MS (ISP) m/z=468.1 [(M+H)$^+$], mp 163° C., was prepared in accordance with the general method of intermediate 1, step D, from 3-amino-5-(4-chlorophenyl)-N-(1,1,1-trifluoro-2-methylpropan-2-yl)-benzamide (0.56 g, 1.58 mmol).

Example 1: N-tert-Butyl-3-(4-chlorophenyl)-5-(2-methyl-pyrazol-3-yl)-benzamide

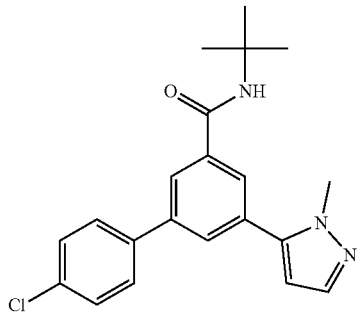 [SMILES: Cn1nccc1-c1cc(C(=O)NC(C)(C)C)cc(-c2ccc(Cl)cc2)c1]

In a sealed tube a mixture of N-tert-butyl-3-(4-chlorophenyl)-5-iodobenzamide (intermediate 1) (103 mg, 0.25 mmol), commercially available 1-methyl-5-(4,4,5,5-tetramethyl-1,3,2-dioxaborolan-2-yl)-1H-pyrazole (67.6 mg, 325 µmol), 1,2-dimethoxyethane (1.67 ml) and 2M sodium carbonate solution (416 µl, 833 µmol) was purged with argon in an ultrasonic bath for 5 min, triphenylphosphine (13.1 mg, 50 µmol) and palladium(II)acetate (5.61 mg, 25 µmol) were added and the reaction mixture was allowed to stir for 16 h at 105° C. The crude reaction mixture was purified by flash chromatography on silica gel [heptane/ethyl acetate (10-60%)] to yield the title compound (73 mg, 79%) as a light brown solid, MS (ISP) m/z=368.2 [(M+H)$^+$], mp 191° C.

Example 2: N-tert-Butyl-3-(2-tert-butyl-pyrazol-3-yl)-5-(4-fluorophenyl)-benzamide

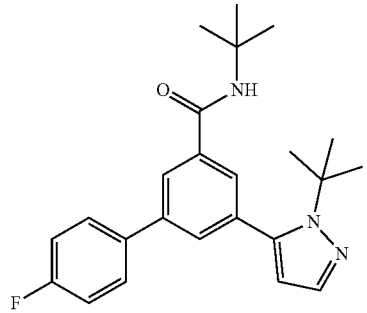 [SMILES: CC(C)(C)NC(=O)c1cc(-c2ccc(F)cc2)cc(-c2ccnn2C(C)(C)C)c1]

The title compound, white solid (61 mg, 62%), MS (ISP) m/z=394.4 [(M+H)$^+$], mp 210° C., was prepared in accordance with the general method of example 1 from N-tert-butyl-3-(4-fluorophenyl)-5-iodobenzamide (intermediate 2) (99.3 mg, 0.25 mmol) and commercially available 1-(tert-butyl)-5-(4,4,5,5-tetramethyl-1,3,2-dioxaborolan-2-yl)-1H-pyrazole (75.0 mg, 0.30 mmol).

Example 3: N-tert-Butyl-3-(2-tert-butyl-pyrazol-3-yl)-5-[4-(trifluoromethyl)-phenyl]-benzamide

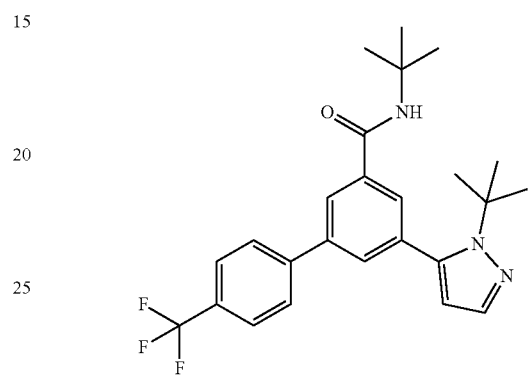

The title compound, off-white solid (63 mg, 57%), MS (ISP) m/z=444.4 [(M+H)$^+$], mp 205° C., was prepared in accordance with the general method of example 1 from N-tert-butyl-3-iodo-5-[4-(trifluoromethyl)-phenyl]-benzamide (intermediate 3) (112 mg, 0.25 mmol) and commercially available 1-(tert-butyl)-5-(4,4,5,5-tetramethyl-1,3,2-dioxaborolan-2-yl)-1H-pyrazole (75.0 mg, 0.30 mmol).

Example 4: N-tert-Butyl-3-(2-tert-butyl-pyrazol-3-yl)-5-(4-chlorophenyl)-benzamide

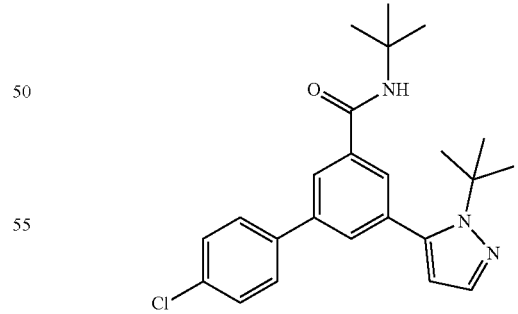

The title compound, white solid (39 mg, 34%), MS (ISP) m/z=410.3 [(M+H)$^+$], mp 209° C., was prepared in accordance with the general method of example 1 from N-tert-butyl-3-(4-chlorophenyl)-5-iodobenzamide (intermediate 1) (103 mg, 0.25 mmol) and commercially available 1-(tert-butyl)-5-(4,4,5,5-tetramethyl-1,3,2-dioxaborolan-2-yl)-1H-pyrazole (75.0 mg, 0.30 mmol).

Example 5: N-tert-Butyl-3-(4-chlorophenyl)-5-(2-propan-2-yl-pyrazol-3-yl)-benzamide

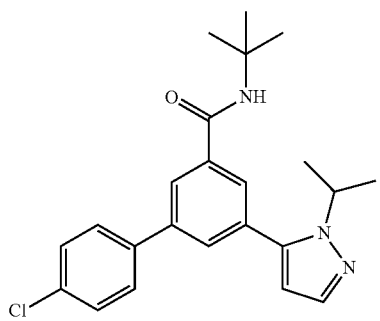 [SMILES: CC(C)n1nccc1-c1cc(C(=O)NC(C)(C)C)cc(-c2ccc(Cl)cc2)c1]

The title compound, white foam (70 mg, 71%), MS (ISP) m/z=396.3 [(M+H)⁺], mp 84° C., was prepared in accordance with the general method of example 1 from N-tert-butyl-3-(4-chlorophenyl)-5-iodobenzamide (intermediate 1) (103 mg, 0.25 mmol) and commercially available (1-isopropyl-1H-pyrazol-5-yl)-boronic acid (46.2 mg, 300 µmol).

Example 6: N-tert-Butyl-3-(4-fluorophenyl)-5-(2-propan-2-yl-pyrazol-3-yl)-benzamide

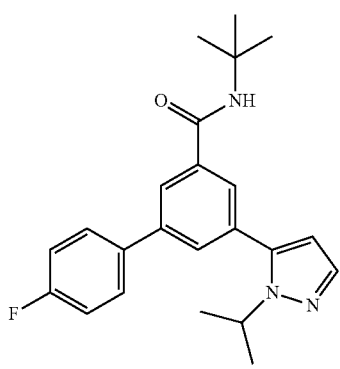 [SMILES: CC(C)n1nccc1-c1cc(C(=O)NC(C)(C)C)cc(-c2ccc(F)cc2)c1]

The title compound, light yellow solid (91 mg, 96%), MS (ISP) m/z=380.3 [(M+H)⁺], mp 161° C., was prepared in accordance with the general method of example 1 from N-tert-butyl-3-(4-fluorophenyl)-5-iodobenzamide (intermediate 2) (99.3 mg, 0.25 mmol) and commercially available (1-isopropyl-1H-pyrazol-5-yl)-boronic acid (50.0 mg, 325 µmol).

Example 7: N-tert-Butyl-3-(2-propan-2-yl-pyrazol-3-yl)-5-[4-(trifluoromethyl)-phenyl]-benzamide

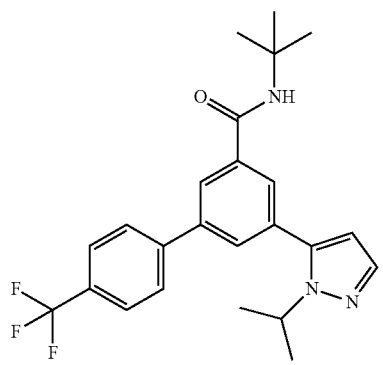 [SMILES: CC(C)n1nccc1-c1cc(C(=O)NC(C)(C)C)cc(-c2ccc(C(F)(F)F)cc2)c1]

The title compound, off-white foam (104 mg, 97%), MS (ISP) m/z=430.3 [(M+H)⁺], mp 81° C., was prepared in accordance with the general method of example 1 from N-tert-butyl-3-iodo-5-[4-(trifluoromethyl)-phenyl]-benzamide (intermediate 3) (112 mg, 0.25 mmol) and commercially available (1-isopropyl-1H-pyrazol-5-yl)-boronic acid (50.0 mg, 325 µmol).

Example 8: N-tert-Butyl-3-(3,4-difluorophenyl)-5-(2-propan-2-yl-pyrazol-3-yl)-benzamide

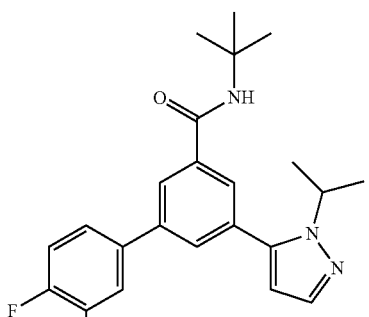

The title compound, off-white solid (95 mg, 96%), MS (ISP) m/z=398.3.3 [(M+H)⁺], mp 82° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available (3,4-difluorophenyl)-boronic acid (51.3 mg, 325 µmol).

Example 9: N-tert-Butyl-3-(4-methylphenyl)-5-(2-propan-2-yl-pyrazol-3-yl)-benzamide

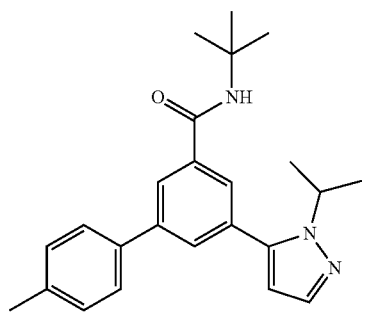 [SMILES: Cc1ccc(-c2cc(C(=O)NC(C)(C)C)cc(-c3ccnn3C(C)C)c2)cc1]

The title compound, light yellow solid (88 mg, 94%), MS (ISP) m/z=376.3 [(M+H)⁺], mp 163° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available p-tolyl-boronic acid (44.2 mg, 325 µmol).

Example 10: N-tert-Butyl-3-(4-propan-2-yl-phenyl)-5-(2-propan-2-yl-pyrazol-3-yl)-benzamide

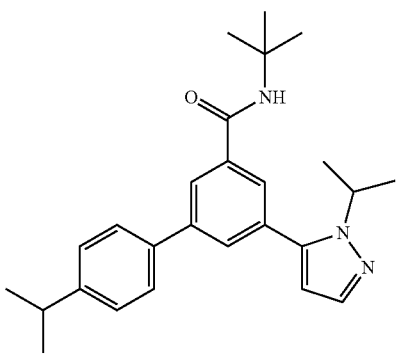 [SMILES: CC(C)c1ccc(-c2cc(C(=O)NC(C)(C)C)cc(-c3ccnn3C(C)C)c2)cc1]

The title compound, white foam (96 mg, 95%), MS (ISP) m/z=404.3 [(M+H)+], mp 86° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available (4-isopropylphenyl)-boronic acid (53.3 mg, 325 µmol).

Example 11: N-tert-Butyl-3-(4-methoxyphenyl)-5-(2-propan-2-yl-pyrazol-3-yl)-benzamide

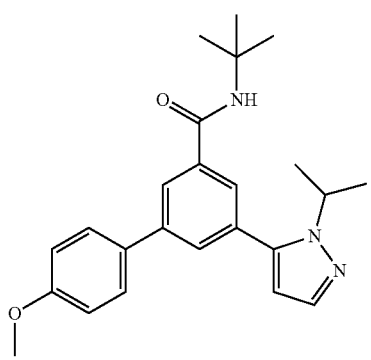 [SMILES: COc1ccc(-c2cc(C(=O)NC(C)(C)C)cc(-c3ccnn3C(C)C)c2)cc1]

The title compound, light brown foam (96 mg, 98%), MS (ISP) m/z=392.3 [(M+H)+], mp 79° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available (4-methoxyphenyl)-boronic acid (49.4 mg, 325 µmol).

Example 12: N-tert-Butyl-3-(3-chloro-4-fluorophenyl)-5-(2-propan-2-yl-pyrazol-3-yl)-benzamide

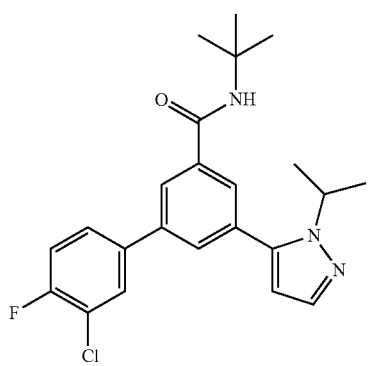 [SMILES: CC(C)n1nccc1-c1cc(C(=O)NC(C)(C)C)cc(-c2ccc(F)c(Cl)c2)c1]

The title compound, off-white foam (103 mg, 99%), MS (ISP) m/z=414.2 [(M+H)+], mp 81° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available (3-chloro-4-fluoro-phenyl)-boronic acid (56.7 mg, 325 µmol).

Example 13: N-tert-Butyl-3-phenyl-5-(2-propan-2-yl-pyrazol-3-yl)-benzamide

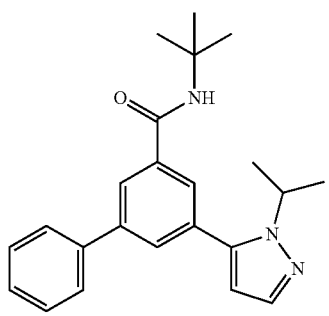 [SMILES: CC(C)n1nccc1-c1cc(C(=O)NC(C)(C)C)cc(-c2ccccc2)c1]

The title compound, light red solid (86 mg, 95%), MS (ISP) m/z=362.3 [(M+H)+], mp 168° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available phenyl-boronic acid (39.6 mg, 325 µmol).

Example 14: N-tert-Butyl-3-(4-cyclopropyl-phenyl)-5-(2-propan-2-yl-pyrazol-3-yl)-benzamide

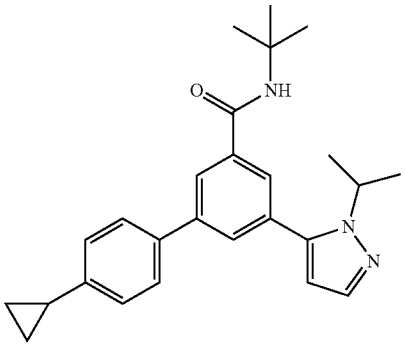 [SMILES: CC(C)n1nccc1-c1cc(C(=O)NC(C)(C)C)cc(-c2ccc(C3CC3)cc2)c1]

The title compound, off-white foam (96 mg, 96%), MS (ISP) m/z=402.3 [(M+H)+], mp 83° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available (4-cyclopropyl-phenyl)-boronic acid (52.6 mg, 325 µmol).

Example 15: N-tert-Butyl-3-(4-fluoro-3-methyl-phenyl)-5-(2-propan-2-yl-pyrazol-3-yl)-benzamide

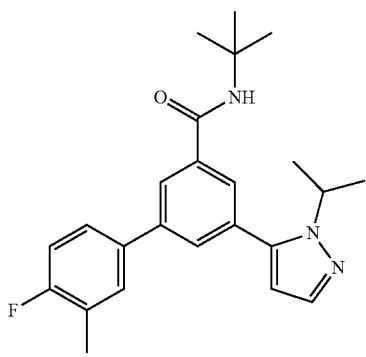 [SMILES: Cc1cc(-c2cc(C(=O)NC(C)(C)C)cc(-c3ccnn3C(C)C)c2)ccc1F]

The title compound, off-white solid (85 mg, 86%), MS (ISP) m/z=394.3 [(M+H)⁺], mp 155° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available (4-fluoro-3-methyl-phenyl)-boronic acid (50.0 mg, 325 μmol).

Example 16: N-tert-Butyl-3-(4-chloro-3-fluoro-phenyl)-5-(2-propan-2-yl-pyrazol-3-yl)-benzamide

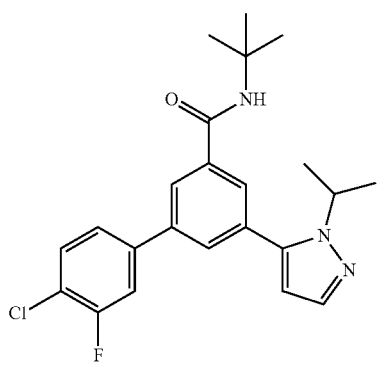 [SMILES: CC(C)n1nccc1-c1cc(C(=O)NC(C)(C)C)cc(-c2ccc(Cl)c(F)c2)c1]

The title compound, off-white foam (98 mg, %), MS (ISP) m/z=414.2 [(M+H)⁺], mp 87° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available (4-chloro-3-fluoro-phenyl)-boronic acid (56.7 mg, 325 μmol).

Example 17: N-tert-Butyl-3-(4-cyano-phenyl)-5-(2-propan-2-yl-pyrazol-3-yl)-benzamide

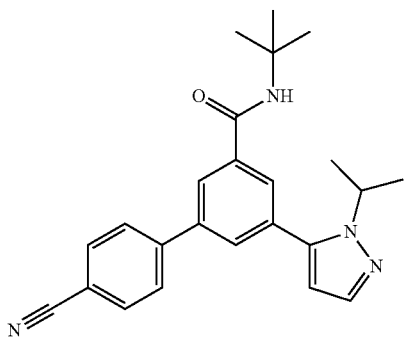 [SMILES: CC(C)n1nccc1-c1cc(C(=O)NC(C)(C)C)cc(-c2ccc(C#N)cc2)c1]

The title compound, light red foam (91 mg, %), MS (ISP) m/z=387.2 [(M+H)⁺], mp 94° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available (4-cyano-phenyl)-boronic acid (47.8 mg, 325 μmol).

Example 18: 3-(2-tert-Butyl-pyrazol-3-yl)-5-(4-chlorophenyl)-N-(2-methyl-butan-2-yl)-benzamide

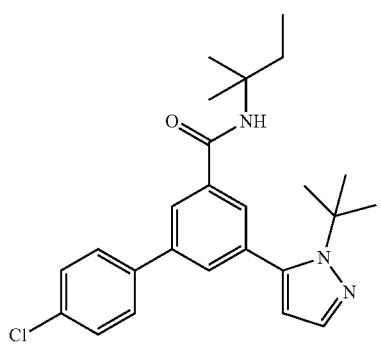 [SMILES: CCC(C)(C)NC(=O)c1cc(-c2ccc(Cl)cc2)cc(-c2ccnn2C(C)(C)C)c1]

The title compound, white solid (40 mg, 38%), MS (ISP) m/z=424.3 [(M+H)⁺], mp 183.5° C., was prepared in accordance with the general method of example 1 from 3-(4-chlorophenyl)-5-iodo-N-(2-methylbutan-2-yl)-benzamide (intermediate 5) (107 mg, 0.25 mmol) and commercially available 1-(tert-butyl)-5-(4,4,5,5-tetramethyl-1,3,2-dioxaborolan-2-yl)-1H-pyrazole (81.3 mg, 325 μmol).

Example 19: 3-(4-Chlorophenyl)-N-(2-methyl-butan-2-yl)-5-(2-propan-2-yl-pyrazol-3-yl)-benzamide

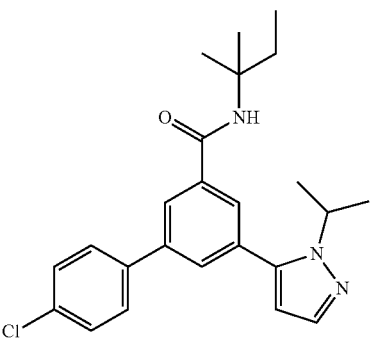 [SMILES: CCC(C)(C)NC(=O)c1cc(-c2ccc(Cl)cc2)cc(-c2ccnn2C(C)C)c1]

The title compound, white foam (80 mg, 78%), MS (ISP) m/z=410.2 [(M+H)⁺], mp 72.5° C., was prepared in accordance with the general method of example 1 from 3-(4-chlorophenyl)-5-iodo-N-(2-methylbutan-2-yl)-benzamide (intermediate 5) (107 mg, 0.25 mmol) and commercially available (1-isopropyl-1H-pyrazol-5-yl)-boronic acid (50.0 mg, 325 μmol).

Example 20: N-tert-Butyl-3-(3-fluoro-4-methyl-phenyl)-5-(2-propan-2-yl-pyrazol-3-yl)-benzamide

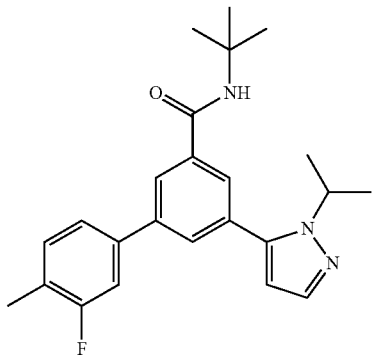 [SMILES: Cc1ccc(-c2cc(C(=O)NC(C)(C)C)cc(-c3ccnn3C(C)C)c2)cc1F]

The title compound, light red foam (93 mg, 95%), MS (ISP) m/z=394.3 [(M+H)⁺], mp 81° C., was prepared in accordance with the general method of example 1 from N-tert-butyl-3-iodo-5-(2-propan-2-yl-pyrazol-3-yl)-benzamide (intermediate 4) (103 mg, 0.25 mmol) and commercially available (3-fluoro-4-methyl-phenyl)-boronic acid (50.0 mg, 325 μmol).

Example 21: 3-(4-Chlorophenyl)-N-(2-cyano-propan-2-yl)-5-(2-propan-2-yl-pyrazol-3-yl)-benzamide

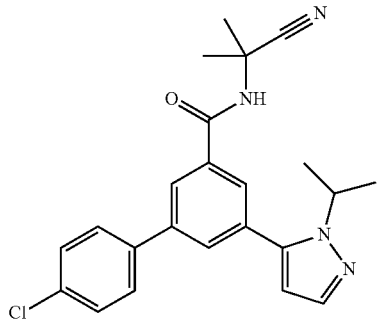 [SMILES: CC(C)n1nccc1-c1cc(C(=O)NC(C)(C)C#N)cc(-c2ccc(Cl)cc2)c1]

The title compound, light yellow foam (80 mg, 79%), MS (ISP) m/z=407.2 [(M+H)⁺], mp 96° C., was prepared in accordance with the general method of example 1 from 3-(4-chlorophenyl)-N-(2-cyano-propan-2-yl)-5-iodo-benzamide (intermediate 6) (106 mg, 0.25 mmol) and commercially available (1-isopropyl-1H-pyrazol-5-yl)-boronic acid (50.0 mg, 325 μmol).

Example 22: 3-(2-tert-Butylpyrazol-3-yl)-5-(4-chlorophenyl)-N-(2-cyanopropan-2-yl)-benzamide

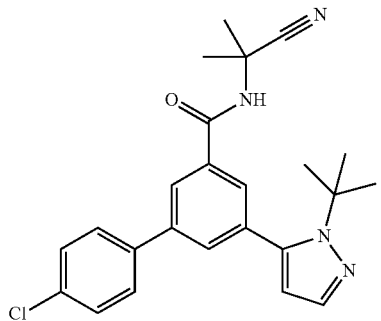 [SMILES: CC(C)(C#N)NC(=O)c1cc(-c2ccc(Cl)cc2)cc(-c2ccnn2C(C)(C)C)c1]

The title compound, white foam (70 mg, 67%), MS (ISP) m/z=421.3 [(M+H)⁺], mp 119° C., was prepared in accordance with the general method of example 1 from 3-(4-chlorophenyl)-N-(2-cyano-propan-2-yl)-5-iodo-benzamide (intermediate 6) (106 mg, 0.25 mmol) and commercially available 1-(tert-butyl)-5-(4,4,5,5-tetramethyl-1,3,2-dioxaborolan-2-yl)-1H-pyrazole (81.3 mg, 325 μmol).

Example 23: N-tert-Butyl-3-(2-cyclopropyl-pyrazol-3-yl)-5-(4-fluorophenyl)-benzamide

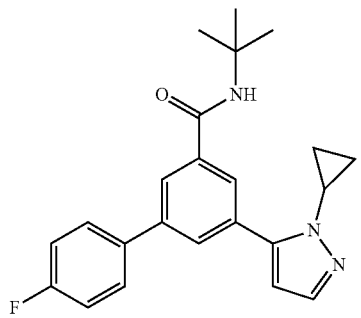 [SMILES: CC(C)(C)NC(=O)c1cc(-c2ccc(F)cc2)cc(-c2ccnn2C2CC2)c1]

The title compound, white foam (70 mg, 74%), MS (ISP) m/z=378.3 [(M+H)⁺], mp 66° C., was prepared in accordance with the general method of example 1 from N-tert-butyl-3-(4-fluorophenyl)-5-iodobenzamide (intermediate 2) (99.3 mg, 0.25 mmol) and commercially available 1-cyclopropyl-5-(4,4,5,5-tetramethyl-1,3,2-dioxaborolan-2-yl)-1H-pyrazole (76.1 mg, 325 μmol).

Example 24: N-tert-Butyl-3-(4-chlorophenyl)-5-(2-ethyl-pyrazol-3-yl)-benzamide

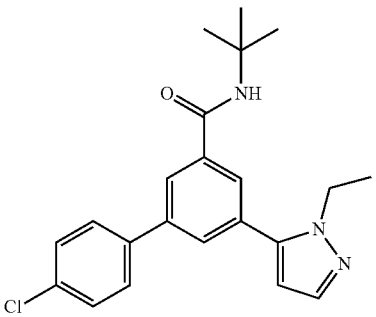 [SMILES: CCn1nccc1-c1cc(C(=O)NC(C)(C)C)cc(-c2ccc(Cl)cc2)c1]

The title compound, off-white foam (74 mg, 78%), MS (ISP) m/z=382.2 [(M+H)⁺], mp 68° C., was prepared in accordance with the general method of example 1 from N-tert-butyl-3-(4-chlorophenyl)-5-iodobenzamide (intermediate 1) (103 mg, 0.25 mmol) and commercially available (1-ethyl-1H-pyrazol-5-yl)-boronic acid (45.5 mg, 325 μmol).

Example 25: N-tert-Butyl-3-(4-chlorophenyl)-5-[2-(cyclopropyl-methyl)-pyrazol-3-yl]-benzamide

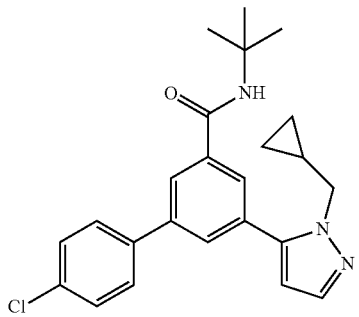 [SMILES: CC(C)(C)NC(=O)c1cc(-c2ccc(Cl)cc2)cc(-c2ccnn2CC2CC2)c1]

The title compound, white solid (84 mg, 82%), MS (ISP) m/z=408.2 [(M+H)⁺], mp 159° C., was prepared in accordance with the general method of example 1 from N-tert-butyl-3-(4-chlorophenyl)-5-iodobenzamide (intermediate 1) (103 mg, 0.25 mmol) and commercially available 1-(cyclopropylmethyl)-5-(4,4,5,5-tetramethyl-1,3,2-dioxaborolan-2-yl)-1H-pyrazole (80.6 mg, 325 µmol).

Example 26: 3-(4-Chlorophenyl)-N-(2-cyclopropyl-propan-2-yl)-5-(2-propan-2-yl-pyrazol-3-yl)-benzamide

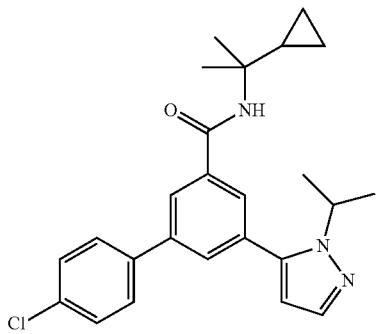 [SMILES: CC(C)n1nccc1-c1cc(C(=O)NC(C)(C)C2CC2)cc(-c2ccc(Cl)cc2)c1]

The title compound, light yellow foam (99 mg, 94%), MS (ISP) m/z=422.3 [(M+H)⁺], mp 169° C., was prepared in accordance with the general method of example 1 from 3-(4-chlorophenyl)-N-(2-cyclopropylpropan-2-yl)-5-iodo-benzamide (intermediate 8) (110 mg, 0.25 mmol) and commercially available (1-isopropyl-1H-pyrazol-5-yl)-boronic acid (50.0 mg, 325 µmol).

Example 27: N-tert-Butyl-3-(2-tert-butyl-pyrazol-3-yl)-5-(4-fluoro-3-methyl-phenyl)-benzamide

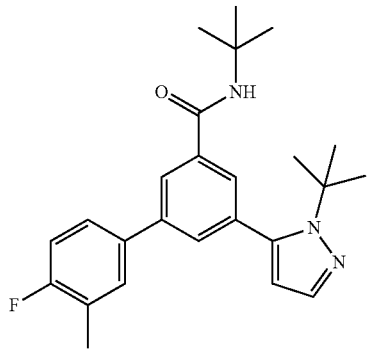 [SMILES: Cc1cc(-c2cc(C(=O)NC(C)(C)C)cc(-c3ccnn3C(C)(C)C)c2)ccc1F]

The title compound, white solid (61 mg, 60%), MS (ISP) m/z=408.3 [(M+H)⁺], mp 186° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available (4-fluoro-3-methyl-phenyl)-boronic acid (50.0 mg, 325 µmol).

Example 28: N-tert-Butyl-3-(2-tert-butyl-pyrazol-3-yl)-5-phenyl-benzamide

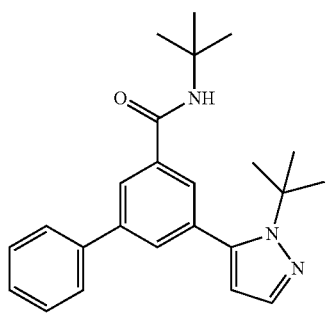 [SMILES: CC(C)(C)NC(=O)c1cc(-c2ccccc2)cc(-c2ccnn2C(C)(C)C)c1]

The title compound, white solid (56 mg, 60%), MS (ISP) m/z=376.3 [(M+H)⁺], mp 199.5° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available phenyl-boronic acid (39.6 mg, 325 µmol).

Example 29: N-tert-Butyl-3-(2-tert-butyl-pyrazol-3-yl)-5-(3-fluoro-4-methyl-phenyl)-benzamide

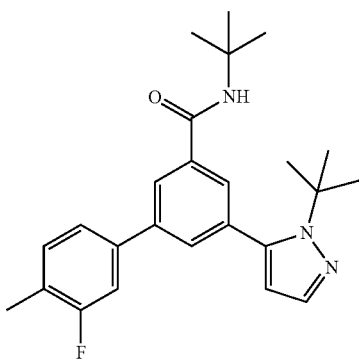 [SMILES: Cc1ccc(-c2cc(C(=O)NC(C)(C)C)cc(-c3ccnn3C(C)(C)C)c2)cc1F]

The title compound, white solid (65 mg, 64%), MS (ISP) m/z=408.3 [(M+H)⁺], mp 202° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available (3-fluoro-4-methyl-phenyl)-boronic acid (50.0 mg, 325 µmol).

Example 30: N-tert-Butyl-3-(2-tert-butyl-pyrazol-3-yl)-5-(4-methyl-phenyl)-benzamide

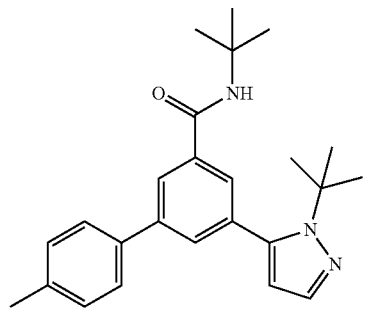 [SMILES: Cc1ccc(-c2cc(C(=O)NC(C)(C)C)cc(-c3ccnn3C(C)(C)C)c2)cc1]

The title compound, white solid (57 mg, 59%), MS (ISP) m/z=390.3 [(M+H)$^+$], mp 193° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available p-tolyl-boronic acid (44.2 mg, 325 μmol).

Example 31: N-tert-Butyl-3-(2-tert-butyl-pyrazol-3-yl)-5-(4-methoxy-phenyl)-benzamide

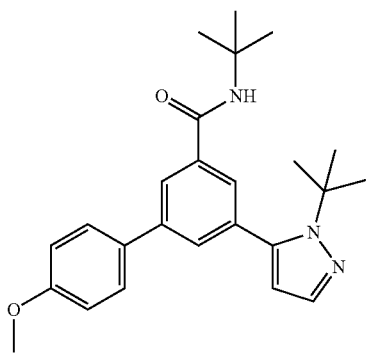 [SMILES: COc1ccc(-c2cc(C(=O)NC(C)(C)C)cc(-c3ccnn3C(C)(C)C)c2)cc1]

The title compound, white solid (68 mg, 67%), MS (ISP) m/z=406.3 [(M+H)$^+$], mp 173° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available (4-methoxyphenyl)-boronic acid (49.4 mg, 325 μmol).

Example 32: N-tert-Butyl-3-(2-tert-butyl-pyrazol-3-yl)-5-(3-chloro-4-fluoro-phenyl)-benzamide

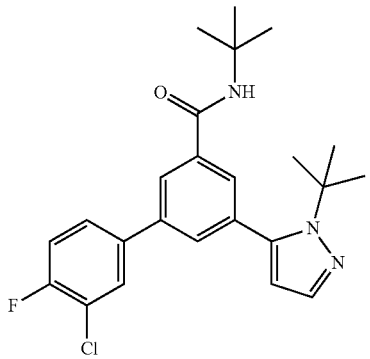 [SMILES: CC(C)(C)NC(=O)c1cc(-c2ccc(F)c(Cl)c2)cc(-c2ccnn2C(C)(C)C)c1]

The title compound, white solid (52 mg, 49%), MS (ISP) m/z=428.3 [(M+H)$^+$], mp 175° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available (3-chloro-4-fluoro-phenyl)-boronic acid (56.7 mg, 325 μmol).

Example 33: N-tert-Butyl-3-(2-tert-butyl-pyrazol-3-yl)-5-(4-chloro-3-fluoro-phenyl)-benzamide

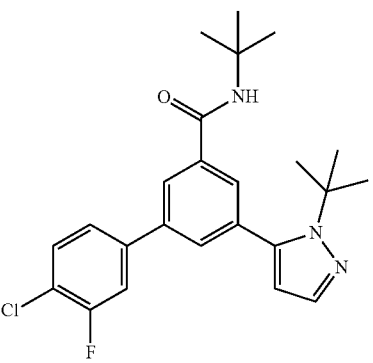 [SMILES: CC(C)(C)NC(=O)c1cc(-c2ccc(Cl)c(F)c2)cc(-c2ccnn2C(C)(C)C)c1]

The title compound, white solid (69 mg, 65%), MS (ISP) m/z=428.3 [(M+H)$^+$], mp 225° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available (4-chloro-3-fluoro-phenyl)-boronic acid (56.7 mg, 325 μmol).

Example 34: N-tert-Butyl-3-(2-tert-butyl-pyrazol-3-yl)-5-(4-propan-2-yl-phenyl)-benzamide

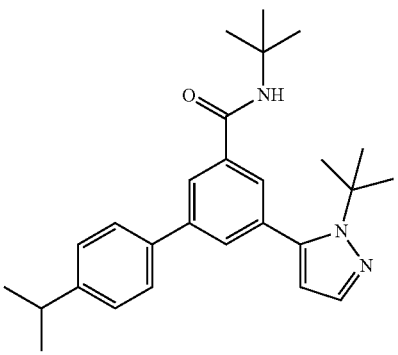 [SMILES: CC(C)c1ccc(-c2cc(C(=O)NC(C)(C)C)cc(-c3ccnn3C(C)(C)C)c2)cc1]

The title compound, white solid (64 mg, 61%), MS (ISP) m/z=418.4 [(M+H)$^+$], mp 209.5° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available (4-isopropylphenyl)-boronic acid (53.3 mg, 325 μmol).

Example 35: 3-(2-tert-Butyl-pyrazol-3-yl)-5-(4-chlorophenyl)-N-(2-cyclopropyl-propan-2-yl)-benzamide

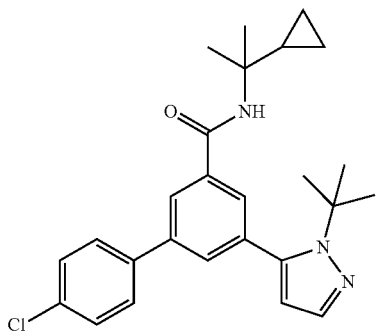 [SMILES: CC(C)(NC(=O)c1cc(-c2ccc(Cl)cc2)cc(-c2ccnn2C(C)(C)C)c1)C1CC1]

The title compound, yellow solid (48 mg, 44%), MS (ISP) m/z=436.3 [(M+H)$^+$], mp 166° C., was prepared in accordance with the general method of example 1 from 3-(4-chlorophenyl)-N-(2-cyclopropylpropan-2-yl)-5-iodobenzamide (intermediate 8) (110 mg, 0.25 mmol) and commercially available 1-(tert-butyl)-5-(4,4,5,5-tetramethyl-1,3,2-dioxaborolan-2-yl)-1H-pyrazole (81.3 mg, 325 μmol).

Example 36: N-tert-Butyl-3-(2-tert-butyl-pyrazol-3-yl)-5-(3,4-difluorophenyl)-benzamide

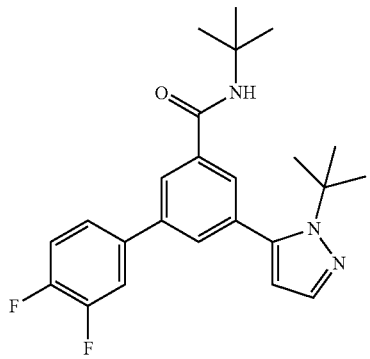

The title compound, white solid (53 mg, 52%), MS (ISP) m/z=412.3 [(M+H)$^+$], mp 197.5° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available (3,4-difluorophenyl)-boronic acid (51.3 mg, 325 μmol).

Example 37: N-tert-Butyl-3-(2-tert-butyl-pyrazol-3-yl)-5-(4-cyclopropyl-phenyl)-benzamide

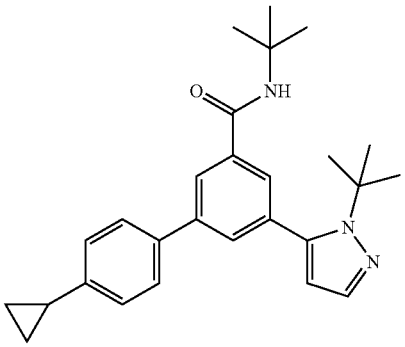 [SMILES: CC(C)(C)NC(=O)c1cc(-c2ccc(C3CC3)cc2)cc(-c2ccnn2C(C)(C)C)c1]

The title compound, white solid (60 mg, 58%), MS (ISP) m/z=416.3 [(M+H)$^+$], mp 198.5° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available (4-cyclopropyl-phenyl)-boronic acid (52.6 mg, 325 μmol).

Example 38: N-tert-Butyl-3-(2-tert-butyl-pyrazol-3-yl)-5-(4-cyano-phenyl)-benzamide

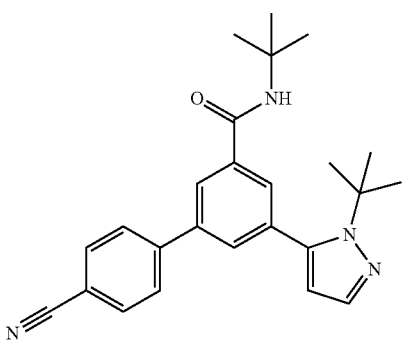 [SMILES: CC(C)(C)NC(=O)c1cc(-c2ccc(C#N)cc2)cc(-c2ccnn2C(C)(C)C)c1]

The title compound, white solid (63 mg, 63%), MS (ISP) m/z=401.3 [(M+H)$^+$], mp 201.5° C., was prepared in accordance with the general method of example 1 from N-tert-butyl-3-(2-tert-butyl-pyrazol-3-yl)-5-iodo-benzamide (intermediate 7) (106 mg, 0.25 mmol) and commercially available (4-cyano-phenyl)-boronic acid (47.8 mg, 325 μmol).

Example 39: 3-(4-Chlorophenyl)-N-(1-hydroxy-2-methyl-propan-2-yl)-5-(2-propan-2-yl-pyrazol-3-yl)-benzamide

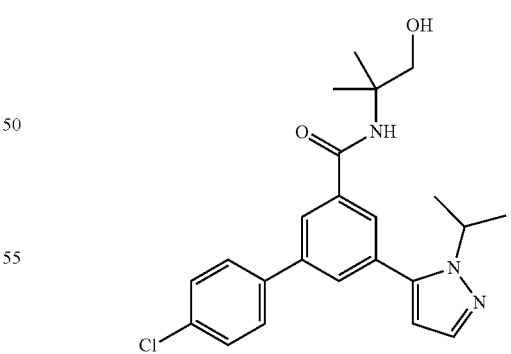

The title compound, off-white foam (80 mg, 78%), MS (ISP) m/z=412.3 [(M+H)$^+$], mp 80.5° C., was prepared in accordance with the general method of example 1 from 3-(4-chlorophenyl)-N-(1-hydroxy-2-methylpropan-2-yl)-5-iodo-benzamide (intermediate 9) (107 mg, 0.25 mmol) and commercially available (1-isopropyl-1H-pyrazol-5-yl)-boronic acid (50.0 mg, 325 μmol).

Example 40: 3-(4-Chlorophenyl)-5-(2-propan-2-yl-pyrazol-3-yl)-N-(1,1,1-trifluoro-2-methyl-propan-2-yl)-benzamide

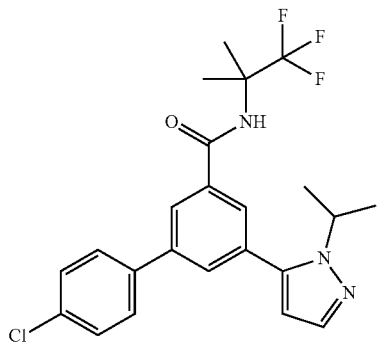 [SMILES: CC(C)n1nccc1-c1cc(C(=O)NC(C)(C)C(F)(F)F)cc(-c2ccc(Cl)cc2)c1]

The title compound, off-white foam (90 mg, 80%), MS (ISP) m/z=450.2 [(M+H)⁺], mp 77.5° C., was prepared in accordance with the general method of example 1 from 3-(4-chlorophenyl)-5-iodo-N-(1,1,1-trifluoro-2-methyl-propan-2-yl)-benzamide (intermediate 10) (117 mg, 0.25 mmol) and commercially available (1-isopropyl-1H-pyrazol-5-yl)-boronic acid (50.0 mg, 325 µmol).

Example 41: 3-(2-tert-Butyl-pyrazol-3-yl)-5-(4-chlorophenyl)-N-(1-hydroxy-2-methylpropan-2-yl)-benzamide

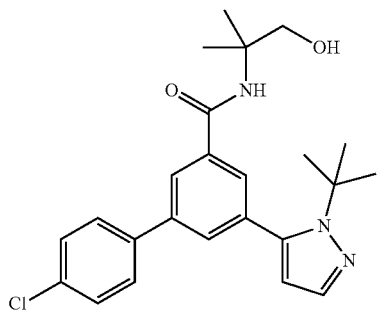 [SMILES: CC(C)(CO)NC(=O)c1cc(-c2ccc(Cl)cc2)cc(-c2ccnn2C(C)(C)C)c1]

The title compound, off-white foam (60 mg, 56%), MS (ISP) m/z=426.3 [(M+H)⁺], mp 83° C., was prepared in accordance with the general method of example 1 from 3-(4-chlorophenyl)-N-(1-hydroxy-2-methylpropan-2-yl)-5-iodo-benzamide (intermediate 9) (107 mg, 0.25 mmol) and commercially available 1-(tert-butyl)-5-(4,4,5,5-tetramethyl-1,3,2-dioxaborolan-2-yl)-1H-pyrazole (81.3 mg, 325 µmol).

Example 42: 3-(2-tert-Butylpyrazol-3-yl)-5-(4-chlorophenyl)-N-(1,1,1-trifluoro-2-methyl-propan-2-yl)-benzamide

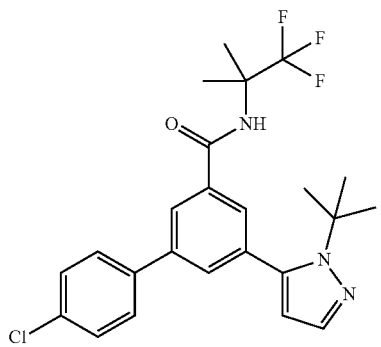 [SMILES: CC(C)(C)n1nccc1-c1cc(C(=O)NC(C)(C)C(F)(F)F)cc(-c2ccc(Cl)cc2)c1]

The title compound, light yellow foam (30 mg, 26%), MS (ISP) m/z=464.4 [(M+H)⁺], mp 81° C., was prepared in accordance with the general method of example 1 from 3-(4-chlorophenyl)-5-iodo-N-(1,1,1-trifluoro-2-methyl-propan-2-yl)-benzamide (intermediate 10) (117 mg, 0.25 mmol) and commercially available 1-(tert-butyl)-5-(4,4,5,5-tetramethyl-1,3,2-dioxaborolan-2-yl)-1H-pyrazole (81.3 mg, 325 µmol).

Example 43: N-tert-Butyl-3-(2-cyclopropyl-pyrazol-3-yl)-5-[4-(trifluoromethyl)-phenyl]-benzamide

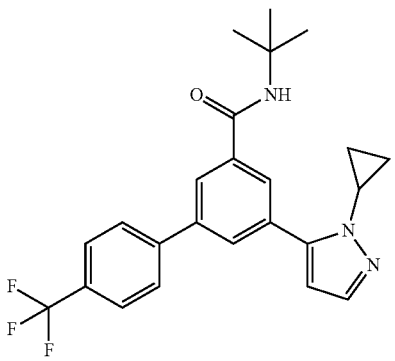 [SMILES: CC(C)(C)NC(=O)c1cc(-c2ccc(C(F)(F)F)cc2)cc(-c2ccnn2C2CC2)c1]

The title compound, white foam (85 mg, 80%), MS (ISP) m/z=428.3 [(M+H)⁺], mp 72° C., was prepared in accordance with the general method of example 1 from N-tert-butyl-3-iodo-5-[4-(trifluoromethyl)-phenyl]-benzamide (intermediate 3) (112 mg, 0.25 mmol) and commercially available 1-cyclopropyl-5-(4,4,5,5-tetramethyl-1,3,2-dioxaborolan-2-yl)-1H-pyrazole (76.1 mg, 325 µmol).

Example 44: N-tert-Butyl-3-[2-(cyclopropylmethyl)-pyrazol-3-yl]-5-[4-(trifluoromethyl)-phenyl]-benzamide

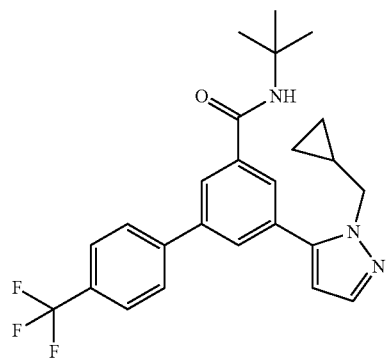 [SMILES: CC(C)(C)NC(=O)c1cc(-c2ccc(C(F)(F)F)cc2)cc(-c2ccnn2CC2CC2)c1]

The title compound, white foam (87 mg, 79%), MS (ISP) m/z=442.3 [(M+H)⁺], mp 69° C., was prepared in accordance with the general method of example 1 from N-tert-butyl-3-iodo-5-[4-(trifluoromethyl)-phenyl]-benzamide (intermediate 3) (112 mg, 0.25 mmol) and commercially available 1-(cyclopropylmethyl)-5-(4,4,5,5-tetramethyl-1,3,2-dioxaborolan-2-yl)-1H-pyrazole (80.6 mg, 325 µmol).

Example 45: N-tert-Butyl-3-(4-chlorophenyl)-5-(2-cyclopropyl-pyrazol-3-yl)-benzamide

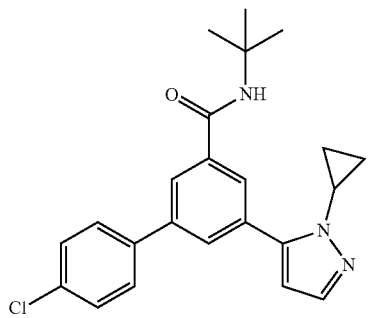 [SMILES: CC(C)(C)NC(=O)c1cc(-c2ccc(Cl)cc2)cc(-c2ccnn2C2CC2)c1]

The title compound, off-white foam (55 mg, 72%), MS (ISP) m/z=394.2 [(M+H)$^+$], mp 72° C., was prepared in accordance with the general method of example 1 from N-tert-butyl-3-(4-chlorophenyl)-5-iodobenzamide (intermediate 1) (80.0 mg, 0.19 mmol) and commercially available 1-cyclopropyl-5-(4,4,5,5-tetramethyl-1,3,2-dioxaborolan-2-yl)-1H-pyrazole (58.9 mg, 0.25 mmol).

Example 46: N-tert-Butyl-3-[2-(cyclopropylmethyl)-pyrazol-3-yl]-5-(4-fluorophenyl)-benzamide

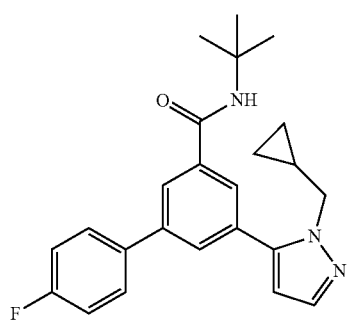 [SMILES: CC(C)(C)NC(=O)c1cc(-c2ccc(F)cc2)cc(-c2ccnn2CC2CC2)c1]

The title compound, white solid (90 mg, 92%), MS (ISP) m/z=392.3 [(M+H)$^+$], mp 188° C., was prepared in accordance with the general method of example 1 from N-tert-butyl-3-(4-fluorophenyl)-5-iodobenzamide (intermediate 2) (99.3 mg, 0.25 mmol) and commercially available 1-(cyclopropylmethyl)-5-(4,4,5,5-tetramethyl-1,3,2-dioxaborolan-2-yl)-1H-pyrazole (80.6 mg, 325 μmol).

Example 47: N-tert-Butyl-3-(2-ethyl-pyrazol-3-yl)-5-(4-fluorophenyl)-benzamide

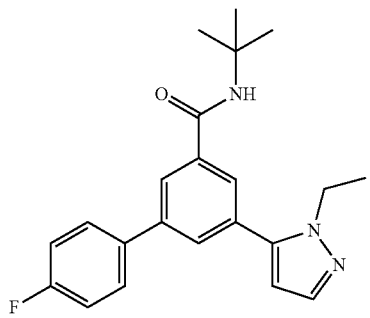 [SMILES: CCn1nccc1-c1cc(C(=O)NC(C)(C)C)cc(-c2ccc(F)cc2)c1]

The title compound, off-white solid (87 mg, 95%), MS (ISP) m/z=366.2 [(M+H)$^+$], mp 162° C., was prepared in accordance with the general method of example 1 from N-tert-butyl-3-(4-fluorophenyl)-5-iodobenzamide (intermediate 2) (99.3 mg, 0.25 mmol) and commercially available (1-ethyl-1H-pyrazol-5-yl)boronic (45.5 mg, 325 μmol).

Example 48: N-tert-Butyl-3-(2-ethyl-pyrazol-3-yl)-5-[4-(trifluoromethyl)-phenyl]-benzamide

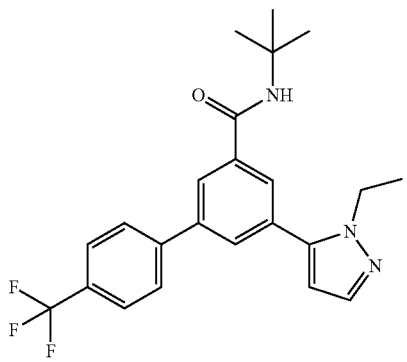 [SMILES: CCn1nccc1-c1cc(C(=O)NC(C)(C)C)cc(-c2ccc(C(F)(F)F)cc2)c1]

The title compound, white foam (67 mg, 65%), MS (ISP) m/z=416.3 [(M+H)$^+$], mp 70° C., was prepared in accordance with the general method of example 1 from N-tert-butyl-3-iodo-5-[4-(trifluoromethyl)-phenyl]-benzamide (intermediate 3) (112 mg, 0.25 mmol) and commercially available (1-ethyl-1H-pyrazol-5-yl)boronic (45.5 mg, 325 μmol).

The invention claimed is:
1. A compound of formula (I):

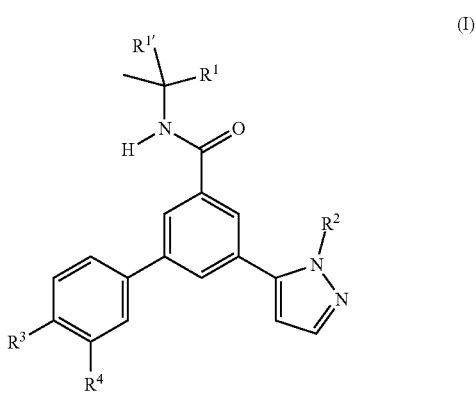

wherein
R$^{1'}$ is methyl;
R$^1$ is selected from the group consisting of
i) methyl,
ii) ethyl,
iii) trifluoromethyl
iv) hydroxymethyl,
v) cyclopropyl, and
vi) cyano;
or R$^{1'}$ and R$^1$ together with the carbon atom to which they are attached form 1,1-dioxo-tetrahydro-thiophen-3-yl;
R$^2$ is selected from the group consisting of
i) hydrogen,
ii) methyl,
iii) ethyl,
iv) isopropyl, v) tert-butyl,
vi) cyclopropyl,
vii) cyclopropylmethyl, and
viii) hydroxymethyl;
R³ is selected from the group consisting of
i) hydrogen,
ii) chloro,
iii) fluoro,
iv) methyl
v) isopropyl,
vi) methoxy,
vii) cyano,
viii) cyclopropyl, and
ix) trifluoromethyl;
R⁴ is selected from the group consisting of
i) hydrogen,
ii) chloro,
iii) fluoro, and
iv) methyl;
or a pharmaceutically acceptable salt thereof.

2. A compound according to claim 1, wherein R¹ is methyl.

3. A compound according to claim 1, wherein R² is selected from the group consisting of
i) methyl,
ii) ethyl,
iii) isopropyl,
iv) tert-butyl,
v) cyclopropyl, and
vi) cyclopropylmethyl.

4. A compound according to claim 1, wherein R³ is selected from the group consisting of
i) hydrogen,
ii) chloro,
iii) fluoro,
iv) methyl
v) isopropyl,
vi) methoxy,
vii) cyano,
viii) cyclopropyl, and
ix) trifluoromethyl.

5. A compound according to claim 1, wherein R³ is selected from the group consisting of
i) chloro,
ii) fluoro,
iii) cyano, and
iv) trifluoromethyl.

6. A compound according to claim 1, wherein R⁴ is H.

7. A compound according to claim 1, wherein R¹' and R¹ are both methyl;
R² is selected from the group consisting of
i) methyl,
ii) ethyl,
iii) isopropyl,
iv) tert-butyl,
v) cyclopropyl, and
vi) cyclopropylmethyl;
R³ is selected from the group consisting of
i) hydrogen,
ii) chloro,
iii) fluoro,
iv) methyl
v) isopropyl,
vi) methoxy,
vii) cyano, and
viii) cyclopropyl R⁴ is selected from the group consisting of
i) hydrogen,
ii) chloro,
iii) fluoro, and
iv) methyl;
or pharmaceutically acceptable salts.

8. A compound according to claim 1, selected from
N-tert-butyl-3-(4-chlorophenyl)-5-(2-methylpyrazol-3-yl)benzamide;
N-tert-butyl-3-(2-tert-butylpyrazol-3-yl)-5-(4-fluorophenyl)benzamide;
N-tert-butyl-3-(2-tert-butylpyrazol-3-yl)-5-[4-(trifluoromethyl)phenyl]benzamide;
N-tert-butyl-3-(2-tert-butylpyrazol-3-yl)-5-(4-chlorophenyl)benzamide;
N-tert-butyl-3-(4-chlorophenyl)-5-(2-propan-2-ylpyrazol-3-yl)benzamide;
N-tert-butyl-3-(4-fluorophenyl)-5-(2-propan-2-ylpyrazol-3-yl)benzamide;
N-tert-butyl-3-(2-propan-2-ylpyrazol-3-yl)-5-[4-(trifluoromethyl)phenyl]benzamide;
N-tert-butyl-3-(3,4-difluorophenyl)-5-(2-propan-2-ylpyrazol-3-yl)benzamide;
N-tert-butyl-3-(4-methylphenyl)-5-(2-propan-2-ylpyrazol-3-yl)benzamide;
N-tert-butyl-3-(4-propan-2-ylphenyl)-5-(2-propan-2-ylpyrazol-3-yl)benzamide;
N-tert-butyl-3-(4-methoxyphenyl)-5-(2-propan-2-ylpyrazol-3-yl)benzamide;
N-tert-butyl-3-(3-chloro-4-fluorophenyl)-5-(2-propan-2-ylpyrazol-3-yl)benzamide;
N-tert-butyl-3-phenyl-5-(2-propan-2-ylpyrazol-3-yl)benzamide;
N-tert-butyl-3-(4-cyclopropylphenyl)-5-(2-propan-2-ylpyrazol-3-yl)benzamide;
N-tert-butyl-3-(4-fluoro-3-methylphenyl)-5-(2-propan-2-ylpyrazol-3-yl)benzamide;
N-tert-butyl-3-(4-chloro-3-fluorophenyl)-5-(2-propan-2-ylpyrazol-3-yl)benzamide;
N-tert-butyl-3-(4-cyanophenyl)-5-(2-propan-2-ylpyrazol-3-yl)benzamide;
3-(2-tert-butylpyrazol-3-yl)-5-(4-chlorophenyl)-N-(2-methylbutan-2-yl)benzamide;
3-(4-chlorophenyl)-N-(2-methylbutan-2-yl)-5-(2-propan-2-ylpyrazol-3-yl)benzamide;
N-tert-butyl-3-(3-fluoro-4-methylphenyl)-5-(2-propan-2-ylpyrazol-3-yl)benzamide;
3-(4-chlorophenyl)-N-(2-cyanopropan-2-yl)-5-(2-propan-2-ylpyrazol-3-yl)benzamide;
3-(2-tert-butylpyrazol-3-yl)-5-(4-chlorophenyl)-N-(2-cyanopropan-2-yl)benzamide;
N-tert-butyl-3-(2-cyclopropylpyrazol-3-yl)-5-(4-fluorophenyl)benzamide;
N-tert-butyl-3-(4-chlorophenyl)-5-(2-ethylpyrazol-3-yl)benzamide;
N-tert-butyl-3-(4-chlorophenyl)-5-[2-(cyclopropylmethyl)pyrazol-3-yl]benzamide;
3-(4-chlorophenyl)-N-(2-cyclopropylpropan-2-yl)-5-(2-propan-2-ylpyrazol-3-yl)benzamide;
N-tert-butyl-3-(2-tert-butylpyrazol-3-yl)-5-(4-fluoro-3-methylphenyl)benzamide;
N-tert-butyl-3-(2-tert-butylpyrazol-3-yl)-5-phenylbenzamide;
N-tert-butyl-3-(2-tert-butylpyrazol-3-yl)-5-(3-fluoro-4-methylphenyl)benzamide;
N-tert-butyl-3-(2-tert-butylpyrazol-3-yl)-5-(4-methylphenyl)benzamide;

N-tert-butyl-3-(2-tert-butylpyrazol-3-yl)-5-(4-methoxyphenyl)benzamide;
N-tert-butyl-3-(2-tert-butylpyrazol-3-yl)-5-(3-chloro-4-fluorophenyl)benzamide;
N-tert-butyl-3-(2-tert-butylpyrazol-3-yl)-5-(4-chloro-3-fluorophenyl)benzamide;
N-tert-butyl-3-(2-tert-butylpyrazol-3-yl)-5-(4-propan-2-ylphenyl)benzamide;
3-(2-tert-butylpyrazol-3-yl)-5-(4-chlorophenyl)-N-(2-cyclopropylpropan-2-yl)benzamide;
N-tert-butyl-3-(2-tert-butylpyrazol-3-yl)-5-(3,4-difluorophenyl)benzamide;
N-tert-butyl-3-(2-tert-butylpyrazol-3-yl)-5-(4-cyclopropylphenyl)benzamide;
N-tert-butyl-3-(2-tert-butylpyrazol-3-yl)-5-(4-cyanophenyl)benzamide;
3-(4-chlorophenyl)-N-(1-hydroxy-2-methylpropan-2-yl)-5-(2-propan-2-ylpyrazol-3-yl)benzamide;
3-(4-chlorophenyl)-5-(2-propan-2-ylpyrazol-3-yl)-N-(1,1,1-trifluoro-2-methylpropan-2-yl)benzamide;
3-(2-tert-butylpyrazol-3-yl)-5-(4-chlorophenyl)-N-(1-hydroxy-2-methylpropan-2-yl)benzamide;
3-(2-tert-butylpyrazol-3-yl)-5-(4-chlorophenyl)-N-(1,1,1-trifluoro-2-methylpropan-2-yl)benzamide;
N-tert-butyl-3-(2-cyclopropylpyrazol-3-yl)-5-[4-(trifluoromethyl)phenyl]benzamide;
N-tert-butyl-3-[2-(cyclopropylmethyl)pyrazol-3-yl]-5-[4-(trifluoromethyl)phenyl]benzamide;
N-tert-butyl-3-(4-chlorophenyl)-5-(2-cyclopropylpyrazol-3-yl)benzamide;
N-tert-butyl-3-[2-(cyclopropylmethyl)pyrazol-3-yl]-5-(4-fluorophenyl)benzamide;
N-tert-butyl-3-(2-ethylpyrazol-3-yl)-5-(4-fluorophenyl)benzamide;
N-tert-butyl-3-(2-ethylpyrazol-3-yl)-5-[4-(trifluoromethyl)phenyl]benzamide;
and/or a pharmaceutically acceptable salt thereof.

9. A compound according to claim 1, selected from
N-tert-butyl-3-(4-chlorophenyl)-5-(2-methylpyrazol-3-yl)benzamide;
N-tert-butyl-3-(2-tert-butylpyrazol-3-yl)-5-(4-fluorophenyl)benzamide;
N-tert-butyl-3-(4-chlorophenyl)-5-(2-propan-2-ylpyrazol-3-yl)benzamide;
N-tert-butyl-3-(4-fluorophenyl)-5-(2-propan-2-ylpyrazol-3-yl)benzamide;
N-tert-butyl-3-(2-propan-2-ylpyrazol-3-yl)-5-[4-(trifluoromethyl)phenyl]benzamide;
N-tert-butyl-3-(2-cyclopropylpyrazol-3-yl)-5-(4-fluorophenyl)benzamide;
N-tert-butyl-3-(4-chlorophenyl)-5-(2-ethylpyrazol-3-yl)benzamide;
N-tert-butyl-3-(4-chlorophenyl)-5-[2-(cyclopropylmethyl)pyrazol-3-yl]benzamide;
N-tert-butyl-3-(2-tert-butylpyrazol-3-yl)-5-(4-cyanophenyl)benzamide;
N-tert-butyl-3-(4-chlorophenyl)-5-(2-cyclopropylpyrazol-3-yl)benzamide;
N-tert-butyl-3-(2-ethylpyrazol-3-yl)-5-(4-fluorophenyl)benzamide;
or a pharmaceutically acceptable salt thereof.

10. A process to prepare a compound according to claim 1 comprising a) the reaction of a compound of formula (II) in the presence of a compound of formula (III), wherein $R^1$, $R^{1'}$, $R^2$, $R^3$ and $R^4$ are as defined in any one of claims 1 to 9;

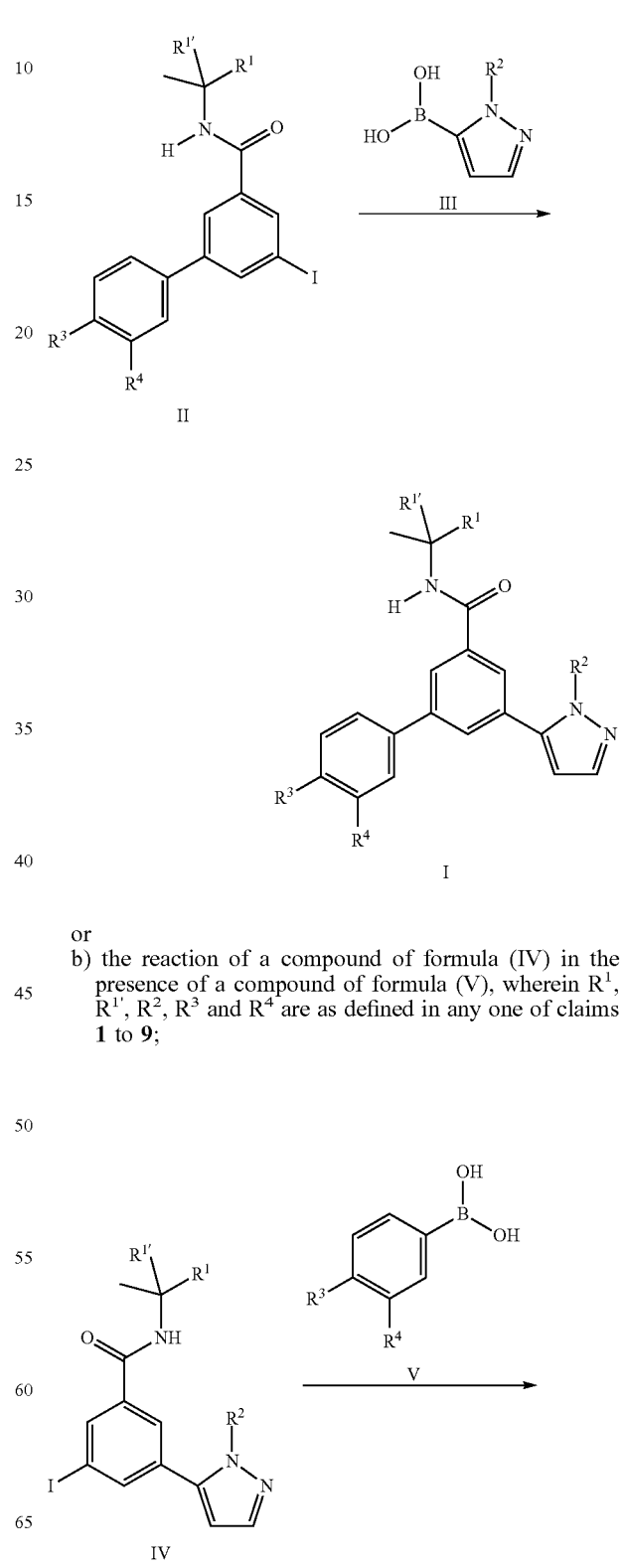

or
b) the reaction of a compound of formula (IV) in the presence of a compound of formula (V), wherein $R^1$, $R^{1'}$, $R^2$, $R^3$ and $R^4$ are as defined in any one of claims 1 to 9;

-continued

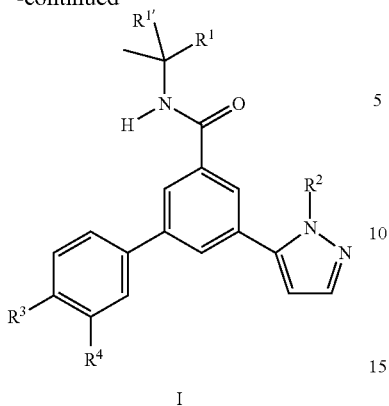

I or c) the reaction of a compound of formula (XVII) in the presence of a compound of formula (VII), wherein $R^1$, $R^{1'}$, $R^2$, $R^3$ and $R^4$ are as defined in any one of claims 1 to 9;

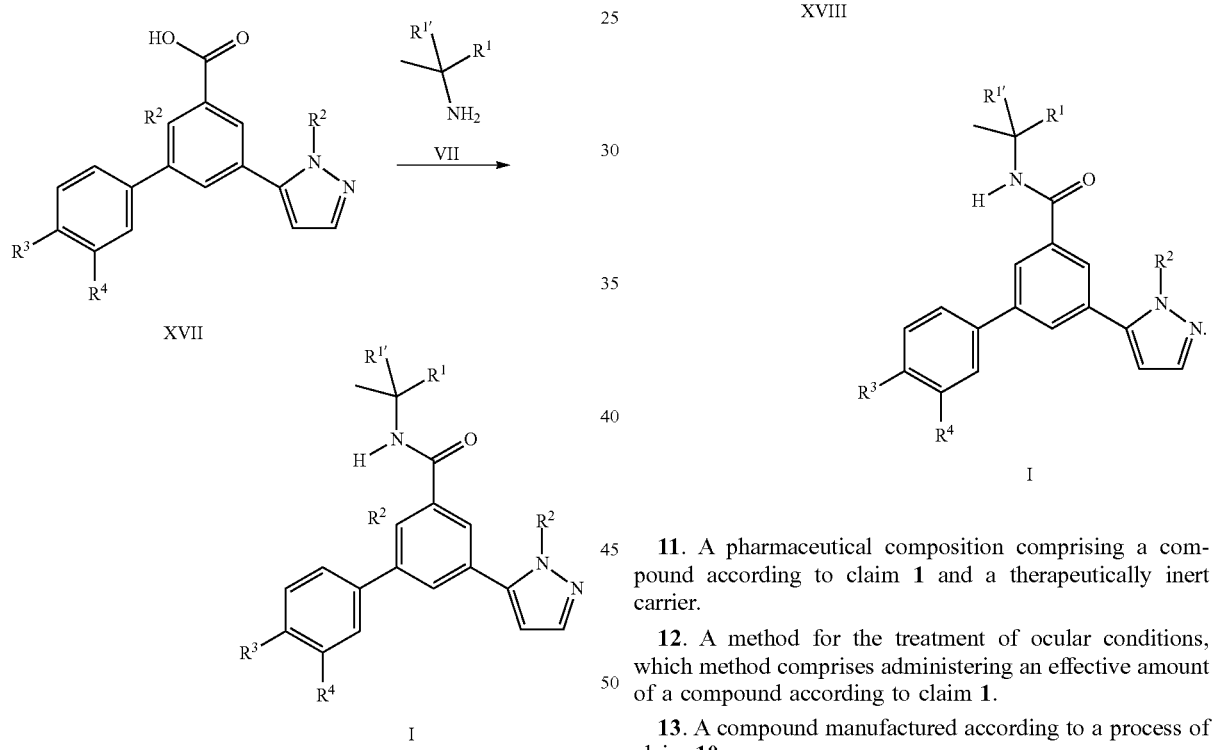

or d) the reaction of a compound of formula (XVIII) in the presence of a compound of formula (XVI), wherein $R^1$, $R^{1'}$, $R^2$, $R^3$ and $R^4$ are as defined in any one of claims 1 to 9.

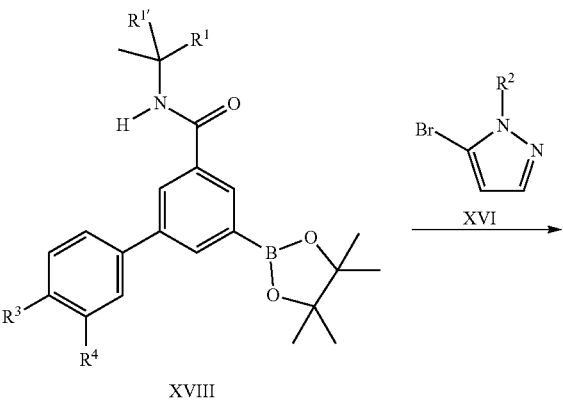

11. A pharmaceutical composition comprising a compound according to claim 1 and a therapeutically inert carrier.

12. A method for the treatment of ocular conditions, which method comprises administering an effective amount of a compound according to claim 1.

13. A compound manufactured according to a process of claim 10.

* * * * *